US010980841B2

(12) United States Patent
Doiron et al.

(10) Patent No.: US 10,980,841 B2
(45) Date of Patent: *Apr. 20, 2021

(54) METHODS AND COMPOSITIONS FOR IN VIVO INDUCTION OF PANCREATIC BETA CELL FORMATION

(71) Applicant: THE BOARD OF REGENTS OF THE UNIVERSITY OF TEXAS SYSTEM, Austin, TX (US)

(72) Inventors: Bruno Doiron, San Antonio, TX (US); Ralph A Defronzo, San Antonio, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/394,312

(22) Filed: Apr. 25, 2019

(65) Prior Publication Data
US 2019/0307809 A1 Oct. 10, 2019

Related U.S. Application Data

(63) Continuation of application No. 15/595,576, filed on May 15, 2017, now Pat. No. 10,293,002, which is a continuation of application No. 14/418,957, filed as application No. PCT/US2013/052820 on Jul. 31, 2013, now Pat. No. 9,649,344.

(60) Provisional application No. 61/678,077, filed on Jul. 31, 2012.

(51) Int. Cl.
*A61K 35/39* (2015.01)
*A61K 31/7088* (2006.01)
*A61K 38/17* (2006.01)
*A61K 38/45* (2006.01)
*C07K 14/47* (2006.01)
*C12N 15/113* (2010.01)
*C12N 9/12* (2006.01)
*C12N 9/16* (2006.01)
*A61K 48/00* (2006.01)

(52) U.S. Cl.
CPC .......... *A61K 35/39* (2013.01); *A61K 31/7088* (2013.01); *A61K 38/1709* (2013.01); *A61K 38/45* (2013.01); *C07K 14/4702* (2013.01); *C12N 9/1205* (2013.01); *C12N 9/16* (2013.01); *C12N 15/1137* (2013.01); *C12Y 207/01002* (2013.01); *C12Y 301/03048* (2013.01); *A61K 48/00* (2013.01); *C12N 2320/31* (2013.01); *C12N 2330/51* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | 435/320.1 |
| 5,139,941 A | 8/1992 | Muzyczka et al. | 435/456 |
| 5,538,880 A | 7/1996 | Lundquist et al. | 800/265 |
| 5,550,318 A | 8/1996 | Adams et al. | 800/300.1 |
| 5,610,042 A | 3/1997 | Chang et al. | 800/288 |
| 5,994,136 A | 11/1999 | Naldini et al. | 435/455 |
| 6,013,516 A | 1/2000 | Verma et al. | 435/325 |
| 8,273,777 B2 | 9/2012 | Shi et al. | 514/365 |
| 9,649,344 B2 | 5/2017 | Doiron et al. | |
| 2005/0042754 A1 | 2/2005 | Miyazaki | 435/455 |

FOREIGN PATENT DOCUMENTS

| | | |
|---|---|---|
| EP | 0273085 | 7/1988 |
| JP | 2003-189875 | 7/2003 |
| JP | 2003-304878 | 10/2003 |
| JP | 2007-61096 | 3/2007 |
| WO | WO/91/016103 | 10/1991 |
| WO | WO/94/009699 | 5/1994 |
| WO | WO/97/026334 | 7/1997 |
| WO | WO/01/053528 | 6/2001 |
| WO | WO/03/080585 | 10/2003 |
| WO | WO/04/050646 | 6/2004 |
| WO | WO/07/010434 | 1/2007 |
| WO | WO/07/075847 | 7/2007 |
| WO | WO/07/122482 | 11/2007 |
| WO | WO/10/022395 | 2/2010 |
| WO | WO/10/089221 | 8/2010 |
| WO | WO/12/046085 | 4/2012 |

OTHER PUBLICATIONS

Huyer, et al. (1997) "Mechanism of Inhibition of Protein-tyrosine Phosphatases by Vanadate and Pervanadate", The Journal of Biological Chemistry, 272(2): 843-51. (Year: 1997).*
Yang, et al. (2006) Inhibition of Protein Tyrosine Phosphatase 1B Lingnans from Myristica fragrans, Phytotherapy Reaserch, 20: 680-82. (Year: 2006).*
Akkarawongsa et al., Antimicrob. Agents and Chemother. 52(6):2120-29, 2008.
Albert and Barabasi, Rev Mod Physics 74:47-97, 2002.
Albert et al., "The topology of the regulatory interactions predicts the expression pattern of the segment polarity genes in *Drosophila melanogaster*." J Theor Biol, vol. 223, 2003, pp. 1-18.
Alonso et al., Diabetes 56:1792-1801, 2007.
Aoki and Matsuda, J Biol. Chem. 275:39718-39726, 2000.
Bernard et al., FASEB J 13:1195-1205, 1999.
Bohnsack et al., "Nutrient regulation of cell cycle progression." Annu Rev Nutr. vol. 24, 2004, pp. 433-453.
Bouwens et al., "Regulation of pancreatic beta-cell mass." Physiol Rev, vol. 85, 2005, pp. 1255-1270.

(Continued)

*Primary Examiner* — Robert M Kelly

(57) ABSTRACT

Embodiments of the invention stimulate three levels of beta cell physiology: (i) glucose metabolism, (ii) membrane receptor function, and (iii) transcriptional factors that result in the in vivo formation of beta cells in the pancreas for the purpose of treating diabetes.

18 Claims, 7 Drawing Sheets

Specification includes a Sequence Listing.

(56) References Cited

OTHER PUBLICATIONS

Combs, et al., "Structure-Based Design and Discovery of Protein Tyrosine Phosphatase Inhibitors Incorporating Novel Isothiazolidinone Heterocyclic Phosphotyrosine Mimetics." J Med Chem. vol. 48, No. 21, 2005, pp. 6544-6548.
Coppieters et al., "Persistent glucose transporter expression on pancreatic beta cells from longstanding type 1 diabetic individuals." Diabetes Metab Res Rev, vol. 27, 2001, pp. 746-754.
Coupar et al., "A general method for the construction of recombinant vaccinia viruses expressing multiple foreign genes." Gene, vol. 68, 1988, pp. 1-10.
Cousin et al., Biochem. J 344:649-658, 1999.
D'Amour et al., "Production of pancreatic hormone-expressing endocrine cells from human embryonic stem cells." Nature Biotech, vol. 24, 2006, pp. 1392-1401.
Derossi et al. J. Biol. Chem. 271:18188-93, 1996.
Doiron and DeFronzo, "A Simple way to Generate Pancreatic Beta Cell Formation In Vivo through 'Cellular Networking, Integration and Processing'" *Journal of Clinical and Molecular Endocrinology*, 2016; 1(2): 1-3.
Doiron et al., "Distinct Effects of Metformin on Pdx-1 Before and After Birth ," Int J Endocrinol Metab. vol. 9, 2011, pp. 356-357.
Doiron et al., "Lentivirus shRNA Grb10 targeting the pancreas induces apoptosis and improved glucose tolerance due to decreased plasma glucagon levels." Diabetologia, vol. 55, 2012, pp. 719-728.
Doiron et al., J Biol Chem. 269: 10213-10216, 1994.
Elliott and O'Hare Cell 88:223-33, 1997.
Eminli et al., Nature Genetics 41:968-976, 2009.
Enver et al. "Stem Cell States, Fates, and the Rules of Attraction" *Cell: Stem Cell Review*, 2009; 4: 387-97.
European Search Report dated Mar. 2, 2016 in European Application No. 13824780.4.
Fraley, et al., Proc. Nat!. Acad. Sci. USA, 76:3348-3352, 1979.
Friedmann, "Progress toward human gene therapy." Science, vol. 244, 1989, pp. 1275-1281.
Futaki et al., "Membrane permeability commonly shared among arginine-rich peptides." J. Mol. Recognit. vol. 16, 2003, pp. 260-264.
Grunhaus et al., "Adenovirus as cloning vectors," Semin. Viral. vol. 3, 1992, pp. 237-252.
Gupta et al., J Biol Chem. 283(47):32462-70, 2008.
Heit et al., "Intrinsic regulators of pancreatic beta-cell proliferation." Annu. Rev Cell Dev. Biol. vol. 22, 2006, pp. 311-338.
Hoorens, et al., J Clin. Invest. 98:1568-1574, 1996.
Horwich et al., J Viral. 64:642-650, 1990.
International Preliminary Report on Patentability in in International Application No. PCT/US2013/052820 dated Feb. 3, 2015.
International Search Report and Written Opinion in International Application No. PCT/US2013/052820 dated Jan. 10, 2014.
Jans FASEB J. 8:841-47, 1994.
Kakazu et al., Invest Opthalmol Vis Sci. 49:2927-2935, 2008.
Kaneda et al., "Increased expression of DNA cointroduced with nuclear protein in adult rat liver." Science. vol. 243, 1989, pp. 375-378.
Kato et al., J Biol. Chem. 266:3361-3364, 1991.
Kitamura et al., "Insulin receptor knockout mice." Annu. Rev. Physiol., vol. 65, 2003, pp. 313-332.
Klein et al., "High-velocity microprojectiles for delivering nucleic acids into living cells," Nature, vol. 327, 1987, pp. 70-73.
Kokryakov et al. "Protegrins: leukocyte antimicrobial peptides that combine features of corticostatic defensins and tachyplesins." FEBS Lett. vol. 327, 1993, pp. 231-236.
Kroon et al., "Pancreatic endoderm derived from human embryonic stem cells generates glucose-responsive insulin-secreting cells in vivo." Nature Biotech, vol. 26, 2008, pp. 443-452.
Lieber et al., "Establishment of a continuous tumor-cell line (panc-1) from a human carcinoma of the exocrine pancreas." Int J Cancer, vol. 15, No. 5, 1975, pp. 741-747.
Minokoshi et al., Journal of Biol. Chem., 278(36): 33609-12, 2003.
Mitanchez et al., "Glucose-stimulated genes and prospects of gene therapy for type I diabetes." Endo Rev, vol. 18, 1997, pp. 520-540.
Newcomb et al., Eukaryot. Cell. 2:143-149, 2003.
Nicolau et al., "Liposome-mediated DNA transfer in eukaryotic cells. Dependence of the transfer efficiency upon the type of liposomes used and the host cell cycle stage." Biochim. Biophys. Acta, vol. 721, 1982, pp. 185-190.
Nicolau et al., "Liposomes as carriers for in vivo gene transfer and expression." Methods Enzymol. vol. 149, 1987, pp. 157-176.
Nielsen et al., Diabetes 50(Suppl. 1): S25-S29, 2001.
Oehlke et al., "Cellular uptake of an alpha-helical amphipathic model peptide with the potential to deliver polar compounds into the cell interior non-endocytically." Biochim. Biophys. Acta. vol. 1414, 1998, pp. 127-139.
Office Action in Chinese Application No. 201380050192.0 dated Jun. 20, 2016.
Pooga et al., FASEB J. 12:67-77, 1988.
Pooga et al., FASEB J. 15:1451-53, 2001.
Roux et al., Proc. Natl. Acad. Sci. USA, 86:9079-83, 1989.
Ruben et al., J Virol. 63:1-8, 1989.
Suzuki et al., J. Biol. Chem. 276:5836-40, 2001.
Tonks, "Protein tyrosine phosphatases: from genes, to function, to disease." Nat Rev. Mol Cell Biol, vol. 7, 2006, pp. 833-846.
Van Assche et al., "A morphological study of the endocrine pancreas in human pregnancy." Br. J Obstet Gynaecol, vol. 85, 1978, pp. 818-820.
Vasavada et al., "Growth factors and beta cell replication." Int J Biochem Cell Biol. vol. 38, 2006, pp. 931-950.
Wang, et al., "Widespread and Stable Pancreatic Gene Transfer by Adeno-Associated Virus Vectors via Different Routes." Diabetes. 55:875-84, 2006.
Wasserman et al., J Exp.Biol. 214:254-262, 2011.
Wei, et al., "Effects of glucokinase activators GKA50 and LY2121260 on proliferation and apoptosis in pancreatic INS-1 beta cells," Diabetologia. vol. 52, 2009, pp. 2142-2150.
Wong, et al., "Appearance of beta-lactamase activity in animal cells upon liposome-mediated gene transfer." Gene, vol. 10, 1980, pp. 87-94.
Wu et al., J Biol. Chem. 262:4429-4432, 1987.
Wyman et al., "Design, synthesis, and characterization of a cationic peptide that binds to nucleic acids and permeabilizes bilayers." Biochemistry, vol. 36, 1997, pp. 3008-3017.
Zhou et al., "In vivo reprogramming of adult pancreatic exocrine cells to beta-cells." Nature vol. 455, 2008, pp. 627-632.
Zufferey, et al., "Woodchuck Hepatitis Virus Posttranscriptional Regulatory Element Enhances Expression of Transgenes Delivered by Retroviral Vectors" J Virology. 73(4):2886-92, 1999.
Miyazuka et al. "Transcription Factor PDX-1 and Diabetes Regenerative Medicine" *Surgery Frontier*, 2003, 10-3, pp. 282-285 (English translation included).

* cited by examiner

Number of Single Insulin-Positive Staining Cells in Exocrine Tissues

SEQUENCE LISTING

<160> NUMBER OF SEQ ID NOS: 8

<210> SEQ ID NO 1
<211> LENGTH: 703
<212> TYPE: DNA
<213> ORGANISM: mus musculus

<400> SEQUENCE: 1

```
tggcttatcg aaattaatac gactcactat agggagaccc aagcttagat ctgtttaaac      60
ctcgagaatt catggctgtg gatactacaa ggaggggagc ccagtcgttg actctggtag     120
agcagatcct ggcagagttc cagctgcagg aggaagacct gaagaaggtg atgagccgga     180
tgcagaagga gatggaccgt ggcctgaagc tggagaccca tcaggaggcc agtgtaaaga     240
tgttgcccac ctacgtgcgt tccacccag aaggctcaga agttggagac tttctctcct      300
tagacctggg aggaaccaac ttcagggtga tgctggtgaa agtgggggag ggggaggcag     360
gacagtggag cgtgaagacg aaacaccaga tgtattccat ccccgaggac gccatgacgg     420
gcactgcgga gatgctcttt gactacatct ctgagtgcat ctctgacttc ctggacaagc     480
atcagatgaa acacaagaaa ctaccctgg gcttcacctt ctccttccct gtaaggcacg     540
aagacataga caagggcatc ctgctcaact ggaccaaggg cttcaaggcc tccggagcag     600
aagggaacaa catcgtggga cttctccgag atgctatcaa gaggagaggg gactttgaga     660
```
tggatgtggt ggcaatggtg aatgacacgg tggccacaat gat         703

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
gccaggacat tcgacatgaa         20

<210> SEQ ID NO 3
<211> LENGTH: 254
<212> TYPE: DNA
<213> ORGANISM: Homo sapiens

<400> SEQUENCE: 3
ccatgaacag tgaggagcag tactacgcgg ccacacagct ctacaaggac ccgtgcgcat         60
tccagagggg cccggtgcca gagttcagcg ctaaccccc tgcgtgcctg tacatgggcc        120
gccagccccc acctccgccg ccaccccagt ttacaagctc gctgggatca ctggagcagg        180
gaagtcctcc ggacatctcc ccatacaaag tgccccgct cgcctccgac gacccggctg        240
gcgctcacct ccac         254

<210> SEQ ID NO 4
<211> LENGTH: 1398
<212> TYPE: DNA
<213> ORGANISM: Homo sapiens

<400> SEQUENCE: 4
atgctggacg acagagccag gatggaggcc gccaagaagg agaaggtaga gcagatcctg         60
gcagagttcc agctgcagga ggaggacctg aagaaggtga tgagacggat gcagaaggag        120
atggaccgcg gcctgaggct ggagacccat gaagaggcca gtgtgaagat gctgcccacc        180
tacgtgcgct ccaccccaga aggctcagaa gtcggggact tcctctcct ggacctgggt        240 ggcactaact tcagggtgat gctggtgaag gtggagaag gtgaggaggg gcagtggagc        300
gtgaagacca acaccagat gtactccatc cccgaggacg ccatgaccgg cactgctgag        360
atgctcttcg actacatctc tgagtgcatc tccgacttcc tggacaagca tcagatgaaa        420
cacaagaagc tgcccctggg cttcaccttc tcctttcctg tgaggcacga agacatcgat        480
aagggcatcc ttctcaactg gaccaagggc ttcaaggcct caggagcaga agggaacaat        540
gtcgtggggc ttctgcgaga cgctatcaaa cggagagggg actttgaaat ggatgtggtg        600
gcaatggtga atgacacggt ggccacgatg atctcctgct actacgaaga ccatcagtgc        660
gaggtcggca tgatcgtggg cacgggctgc aatgcctgct acatggagga gatgcagaat        720
gtggagctgg tgagggga cgaggccgc atgtgcgtca ataccgagtg ggcgccttc        780 ggggactccg gcgagctgga cgagttcctg ctggagtatg accgcctggt ggacgagagc        840
tctgcaaacc ccggtcagca gctgtatgag aagctcatag gtggcaagta catgggcgag        900
ctggtgcggc ttgtgctgct caggctcgtg gacgaaaacc tgctcttcca cggggaggcc        960
tccgagcagc tgcgcacacg cggagccttc gagacgcgct tcgtgtcgca ggtggagagc       1020
gacacgggcg accgcaagca gatctacaac atcctgagca cgctggggct gcgaccctcg       1080
accaccgact cgacatcgt gcgccgcgcc tgcgagagcg tgtctacgcg cgctgcgcac       1140
atgtgctcgg cggggctggc gggcgtcatc aaccgcatgc gcgagagccg cagcgaggac       1200

```
gtaatgcgca tcactgtggg cgtggatggc tccgtgtaca agctgcaccc cagcttcaag    1260
gagcggttcc atgccagcgt gcgcaggctg acgcccagct gcgagatcac cttcatcgag    1320
tcggaggagg gcagtggccg gggcgcggcc ctggtctcgg cggtggcctg taagaaggcc    1380
tgtatgctgg gccagtga                                                  1398
```

<210> SEQ ID NO 5
<211> LENGTH: 465
<212> TYPE: PRT
<213> ORGANISM: Homo sapiens

<400> SEQUENCE: 5

```
Met Leu Asp Asp Arg Ala Arg Met Glu Ala Ala Lys Lys Glu Lys Val
1               5                  10                  15

Glu Gln Ile Leu Ala Glu Phe Gln Leu Gln Glu Glu Asp Leu Lys Lys
            20                  25                  30

Val Met Arg Arg Met Gln Lys Glu Met Asp Arg Gly Leu Arg Leu Glu
        35                  40                  45

Thr His Glu Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Glu
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Trp Thr Lys Gly Phe Lys Ala Ser Gly Ala
                165                 170                 175

Glu Gly Asn Asn Val Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp His Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asp Ser Gly Glu Leu Asp Glu Phe Leu Leu Glu
            260                 265                 270

Tyr Asp Arg Leu Val Asp Glu Ser Ser Ala Asn Pro Gly Gln Gln Leu
        275                 280                 285

Tyr Glu Lys Leu Ile Gly Gly Lys Tyr Met Gly Glu Leu Val Arg Leu
    290                 295                 300

Val Leu Leu Arg Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335
```

```
Gln Val Glu Ser Asp Thr Gly Asp Arg Lys Gln Ile Tyr Asn Ile Leu
            340                 345                 350

Ser Thr Leu Gly Leu Arg Pro Ser Thr Thr Asp Cys Asp Ile Val Arg
            355                 360                 365

Arg Ala Cys Glu Ser Val Ser Thr Arg Ala Ala His Met Cys Ser Ala
            370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Ser Cys Glu Ile Thr Phe Ile Glu Ser Glu Glu Gly Ser Gly Arg Gly
            435                 440                 445

Ala Ala Leu Val Ser Ala Val Ala Cys Lys Lys Ala Cys Met Leu Gly
            450                 455                 460

Gln
465

<210> SEQ ID NO 6
<211> LENGTH: 283
<212> TYPE: PRT
<213> ORGANISM: Homo sapiens

<400> SEQUENCE: 6

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro Pro His
            35                  40                  45

Pro Phe Pro Gly Ala Leu Gly Ala Leu Glu Gln Gly Ser Pro Pro Asp
        50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
            115                 120                 125

Ala Trp Lys Gly Gln Trp Ala Gly Gly Ala Tyr Ala Ala Glu Pro Glu
        130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Asp Lys Lys
            195                 200                 205

Arg Gly Gly Gly Thr Ala Val Gly Gly Gly Val Ala Glu Pro Glu
        210                 215                 220

Gln Asp Cys Ala Val Thr Ser Gly Glu Glu Leu Leu Ala Leu Pro Pro
```

```
                225                 230                 235                 240
Pro Pro Pro Pro Gly Gly Ala Val Pro Pro Ala Ala Pro Val Ala Ala
                    245                 250                 255

Arg Glu Gly Arg Leu Pro Pro Gly Leu Ser Ala Ser Pro Gln Pro Ser
                260                 265                 270

Ser Val Ala Pro Arg Arg Pro Gln Glu Pro Arg
            275                 280

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Tyr Gly Arg Lys Lys Arg Arg Gln Arg Arg Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Gly Arg Lys Lys Arg Arg Gln Arg Arg Arg
1               5                   10
```

//METHODS AND COMPOSITIONS FOR IN VIVO INDUCTION OF PANCREATIC BETA CELL FORMATION

PRIORITY CLAIM

This application is a continuation from U.S. application Ser. No. 15/595,576 filed May 15, 2017 (now U.S. Pat. No. 10,293,002), which is a continuation from U.S. application Ser. No. 14/418,957 filed Feb. 2, 2015 (now U.S. Pat. No. 9,649,344), which is a 371 national phase from WO Application PCT/US2013/052820 filed Jul. 31, 2013, which claims priority to U.S. Provisional Application 61/678,077 filed Jul. 31, 2012; each of which is incorporated herein by reference.

REFERENCE TO SEQUENCE LISTING

A sequence listing required by 37 CFR 1.821-1.825 is being submitted electronically with this application. The sequence listing is incorporated herein by reference.

BACKGROUND

Most medical drug treatments have utilized a reductionist approach: one molecule for one cellular pathophysiological condition. Although the reductionist approach has proven successful for monogenic diseases, it has failed for complex diseases. Physicians have recognized that a combination of approaches is required to treat complex disorders such as type 1 or type 2 diabetes. One treatment for diabetes is the administration of insulin injections, which dates back to 1922. However, insulin injections do not stop the development of diabetic complications (e.g., retinopathy, neuropathy, nephropathy, cardiovascular disease, and stroke) in many type 1 and type 2 diabetic patients. The treatment cost of these diabetic complications is enormous and contributes in a major way to the increased cost health care in diabetic patients.

Although advances have been made in biomedical research, scientists and clinicians are still looking for effective treatments for diabetes. In certain forms of diabetes beta cells are damaged, deficient, or depleted. Potential treatments for diabetes include drug-based therapies and cell-based therapies, both of which have their limitations. Drug-based therapies usually treat symptoms only and patients are chronically dependent on them. Cell-based therapies are hampered by the scarcity of cells and their source, immune rejection, and high manufacturing and distribution costs.

Cell-based therapy is one approach to the treatment of diabetes and other conditions in which a reduction in pancreatic beta cell number or beta cell function is causative or contributory (D'Amour et al., Nature Biotech 24:1392-1401, 2006; Kroon et al., Nature Biotech 26:443-452, 2008). Multicomponent cocktails is one method for reproducing embryonic precursors of beta cells, for example a cocktail of transcriptional factors has been used in stem cell research (Eminli et al., Nature Genetics 41:968-976, 2009) or a viral vector cocktail has been used more recently in the mouse (Zhou et al., Nature 455: 627-632, 2008). In general these cells are not fully developed in their response to glucose, and although the cells contain and express insulin, they fail to secrete insulin in the presence of glucose or in response to changes in glucose concentration.

Thus, there remains a need for methods of treating diabetes, such as producing beta cells that express and secret insulin in vivo in a subject.

SUMMARY

The methods described herein induce pancreatic beta cell formation in vitro or in vivo. In certain aspects the methods induce pancreatic beta cell formation in adult subjects without dedifferentiating cells to recapitulate the embryonic pathway. In further aspects the methods induce pancreatic beta cell formation in cells that are at various stages of differentiation. In other aspects the methods can be used to in vitro to induce beta cell formation. Certain embodiments of the approach described herein specifically target the post-embryonic induction of pancreatic beta cell formation without reproducing the embryonic formation process of the pancreas—the embryonic formation process leads to the generation of multiple pancreatic endocrine cell types. The ability to generate new beta cells in vivo in adult subjects can provide a novel therapeutic approach for the treatment of patients with type 1 and 2 diabetes mellitus, as well as other types of diabetes. The ability to increase the number of pancreatic beta cells in adult subjects can be therapeutic, prophylactic, and/or curative in regards to diabetes.

Certain embodiments are directed to compositions and methods that modulate and integrate three levels of beta cell physiology: (i) glucose metabolism, (ii) membrane receptor function, and (iii) transcriptional factors. In certain aspects, the methods described herein target post-embryonic induction processes of pancreatic beta cell formation. Since the embryonic process leads to multiple endocrine cell types, the post-embryonic methods described herein are designed to induce primarily or only the formation of beta cells. In certain aspects beta cells are formed in vivo in organs or tissues, such as the pancreas, or in vitro without causing formation of detectable levels of other endocrine cell types (e.g., alpha cells that secrete glucagon or delta cells that secrete somatostatin). The inventors are not aware of any reports in which pancreatic beta cell formation is induced in vivo in an adult subject without inducing other pancreatic endocrine cells types. This ability to generate beta cells in vivo in adult subjects provides a novel therapeutic approach for the treatment of patients with type 1 and 2 diabetes mellitus, as well as other types of diabetes.

Certain embodiments employ a gene transfer approach to modulate intracellular targets for pancreatic beta cell formation. Other embodiments use therapeutic agents that mimic the cellular process modulated by the gene transfer methodology. Still other embodiments use a combination of gene transfer and therapeutic agents.

In certain aspects, glucokinase (GK) (GenBank Accession No. NP_034422.2 (GI: 31982798) or NP_000153.1 (GI: 4503951), which is incorporated herein by reference in its entirety as of the application filing date), functional segments or variants thereof, or an activator of GK activity is provided to increase the glucose metabolic rate. Use of other GK nucleic acids transcribed from the GK gene (see GenBank accession NG_008847.1, which is incorporated herein by reference) is also contemplated. In certain aspects a variant of GK that maintains GK enzymatic activity can also be used. In a further aspect, an inhibitor of protein tyrosine phosphatase 1B (PTB1B) (e.g., an inhibitory RNA, antisense DNA, small molecule inhibitor, etc.) is provided to increase tyrosine kinase receptor or tyrosine kinase associated receptor activity. In still a further aspect, Pdx-1 (GenBank Accession No. NP_000200 (GI: 4557673), which is incorporated herein by references as of the application filing date), a functional segment or variant thereof, or an activator of Pdx-1 activity is provided to target genes involved in beta cell formation. In certain aspects a variant of Pdx-1 that maintains Pdx-1 transcription activating abilities can also be used. Use of other Pdx-1 nucleic acids transcribed from the Pdx-1 gene (see GenBank accession NG_008183) is also contemplated. In certain aspects, a nucleic acid encoding a protein of interest is administered. In a further aspect, each protein or inhibitor is comprised in an individual and separate expression cassette or expression vector. In other aspects, two or more proteins are encoded in a single expression cassette or expression vector.

In certain aspects the beta cell inducing agent(s) are administered directly to the pancreas. In certain aspects, the beta cell inducing composition(s) are administered via the pancreatic duct. In a further aspect, beta cell inducing agents are administered orally or intravascularly.

In a further aspect the beta cell inducing agent(s) are administered to a cell in vitro. In certain aspect the cell treated in vitro are cells that are heterologous or autologous to the subject being treated. In one aspect autologous cells are isolated from a patient, administered the inducing agent(s), and the in vitro treated cells are then implanted in the patient. In other aspects a heterologous cell is obtained, administered the inducing agent(s), and the in vitro treated cells are then implanted in the patient.

In certain aspects, an organ, tissue, or cell target is one that can be induced to sense glucose level and secrete insulin. In certain aspects, a target cell or tissue exhibits the ability to induce or be engineered for expression of Glut 2 and/or Glucokinase; expression of proinsulin; and expression of protein convertases to cleave the proinsulin. Cells are present in the human body that have at least two characteristics of a beta cell. A gut K cell is one example of such a cell. Gut K cells express Glut 2, glucokinase, and protein convertase, therefore inducement of insulin expression is needed. In another example, liver cells also express Glut 2 and glucokinase.

Certain embodiments are directed to methods of inducing beta cell formation from post-embryonic pancreatic cells in vivo. In certain aspects, the method includes providing to a pancreas in vivo, a combination of (i) a first agent that increases glucokinase (GK) levels or activity, (ii) a second agent that increases tyrosine receptor kinase activity, and (iii) a third agent that increases Pdx-1 mediated transcription.

In certain aspects the first agent is a nucleic acid encoding glucokinase. The nucleic acid encoding glucokinase can be incorporated in a viral vector. In certain aspects, the viral vector is a lentivirus vector or other nucleic acid delivery vector or particle. The nucleic acid can comprise a posttranscriptional regulatory element 3' of the coding sequence, e.g., a posttranscriptional regulatory element of woodchuck hepatitis virus (WPRE). In certain embodiments a polypeptide comprising a protein transduction domain can be administered to a cell or subject. In certain aspect glucokinase is provided as a recombinant protein fusion comprising protein transduction domains. Protein transduction domains (PTDs or cell permeable proteins (CPP) or membrane translocating sequences (MTS)) are small peptides that are able to ferry much larger molecules into cells independent of classical endocytosis. Many known PTDs bind to the same surface molecules (Heparan Sulphate Proteoglycans, HSPG) before internalization, and that internalization is dependent on these molecules. In further aspects, the first agent can be a small molecule activator of glucokinase. An activator of glucokinase can include, but is not limited to R1440, R00281675, R04389620 (Piragliatin), LY2121260, PSN-GK1, or GKA-50.

In certain aspects, the second agent is an inhibitor of protein tyrosine phosphatase 1B. The protein tyrosine phosphatase 1B inhibitor can be an shRNA inhibitor of protein tyrosine kinase phosphatase 1B. In certain aspects, the protein tyrosine phosphatase 1B inhibitor can be, but is not limited to Wyeth Research Inc., 32D; antisense ISIS-PTP1BRX; Abbott Laboratories, Inc., Isoxazole™; Abbott Laboratories, Inc., antisense oligonucleotides designed to downregulate expression of PTP1B; Merck Frosst Center for Therapeutic Research, selective inhibitors of PTP1B compound 1 and 3; Incyte Corporation, Inc., (S)-isothiazolidinone ((S)-IZD) heterocyclic phosphotyrosine; or Affymax, Inc., triaryl sulfonamide based PTP1B inhibitors.

In still further aspects, the third agent is a beta cell selective transcriptional activator. In certain aspects the transcriptional activator is a nucleic acid encoding Pdx-1. In certain aspect a transcriptional activator is administered to a cell or subject as a recombinant protein fusion with a protein transduction domain. In certain aspects other transcriptional activators used alone or in combination with one or more of NeuroD, Isl1, Nkx6.1, and/or Pax4 can be used. In a further embodiment, the compound troglitazone can be provided in place of or in conjunction with Pdx-1 transcriptional activation.

In certain aspects, the first, second, and third agents are provided in a single composition. In another aspect, the first, second, and third agents are provided separately. The agents can be administered almost simultaneously or within a 1, 2, 3, 4, 5, 6, 7, 8, 9, or 10 minute(s) or hour(s) administration window. In certain embodiments the first, second, and third agent are provided sequentially. In other embodiments the first, second, and third agent are provided simultaneously. In certain embodiments, the first and second agents, first and third agents, or the second and third agents are the same agent.

In certain aspects, the first, second, and third agent are provided by injection or infusion into the pancreas, or other target organ or tissue. In a further aspect, injection or infusion into the pancreas is through the pancreatic duct.

Other embodiments include methods of treating diabetes comprising: providing a therapeutic composition to a pancreas or other organ or tissue in vivo comprising the agents described above. In certain aspects the therapeutic composition comprises (i) glucokinase expression cassette configured to express a functional glucokinase protein, (ii) a tyrosine phosphatase 1B inhibitor, and (iii) a Pdx-1 expression cassette configured to express a functional Pdx-1 protein, wherein pancreatic beta cells are induced. In a further embodiment, the compounds troglitazone can be provided in conjunction with Pdx-1.

Certain embodiments include methods of treating diabetes comprising: obtaining a target cell heterologous to a patient or isolating a autologous target cell from a patient and providing a therapeutic composition to the cell in vitro comprising the agents described above. In certain aspects the therapeutic composition comprises (i) glucokinase expression cassette configured to express a functional glucokinase protein, (ii) a tyrosine phosphatase 1B inhibitor, and (iii) a Pdx-1 expression cassette configured to express a functional Pdx-1 protein, wherein pancreatic beta cells are induced. In a further embodiment, the compounds troglitazone can be provided in conjunction with Pdx-1. The methods further comprise implanting the treated target cell in a patient.

In certain aspects, one, two, or more nucleic acids (i.e., genes) can be used. In certain aspects, three nucleic acids are used. In a further aspect, one, two, or three nucleic acids can be combined with one or more chemical agent. In still further aspects, chemical agents that positively or negatively modulate the target pathways can be used without nucleic acids.

In certain embodiments, chemical agent combinations can include, but are not limited to chemical agent activators of GK in combination with chemical agent inhibitors of PTB1B and/or chemical agent activators of Pdx-1; or chemical agent activators of Pdx-1 with chemical agent inhibitors of PTB1B.

In certain embodiments, nucleic acids can be used in combination with chemical agents. In certain aspects, one or more of a GK gene, PTB1B inhibitory nucleic acid, and/or a Pdx-1 activating nucleic acid can be used in combination with one or more chemical agent PTB1B inhibitor, chemical agent GK activator, and/or chemical agent Pdx-1 activator. As used herein, the gene can refer to a nucleic acid encoding a therapeutic nucleic acid such as GK gene encoding the GK enzyme, the PTB1B gene encoding an inhibitory nucleic acid, or a Pdx-1 encoding an activator of the Pdx-1 pathway.

Various combinations of agents include, but are not limited to chemical agent GK activator(s)+chemical agent PTP1B inhibitor(s); chemical agent GK activator(s)+chemical agent PTP1B inhibitor(s)+chemical agent Pdx-1 activator(s); chemical agent Pdx-1 activator(s)+chemical agent PTP1B inhibitor(s); GK gene+PTP1B gene; GK gene+chemical agent PTP1B inhibitor(s); GK gene+PTP1B gene+chemical agent PTP1B inhibitor(s); GK gene+chemical agent GK activator(s)+PTP1B gene; GK gene+chemical agent GK activator(s)+PTP1B gene+chemical agent PTP1B inhibitor(s); GK gene+chemical agent GK activator(s)+chemical agent PTP1B inhibitor(s); chemical agent GK activator(s)+PTP1B gene; chemical agent GK activator(s)+chemical agent PTP1B inhibitor(s); chemical agent GK activator(s)+PTP1B gene+chemical agent PTP1B inhibitor(s); GK gene+PTP1B gene+Pdx-1 gene; GK gene+chemical agent GK activator(s)+PTP1B gene+Pdx-1 gene; GK gene+chemical agent GK activator (s)+PTP1B gene+chemical agent PTP1B inhibitor(s)+Pdx-1 gene; GK gene+chemical agent GK activator(s)+PTP1B gene+chemical agent PTP1B inhibitor(s)+Pdx-1 gene+chemical agent Pdx-1 activator; GK gene+chemical agent GK activator(s)+PTP1B gene+chemical agent PTP1B inhibitor(s)+chemical agent Pdx-1 activator; chemical agent GK activator(s)+PTP1B gene+Pdx-1 gene; chemical agent GK activator(s)+PTP1B gene+chemical agent PTP1B inhibitor(s)+Pdx-1 gene; chemical agent GK activator(s)+PTP1B gene+chemical agent PTP1B inhibitor(s)+Pdx-1 gene+chemical agent Pdx-1 activator(s); chemical agent GK activator (s)+chemical agent PTP1B inhibitor(s)+chemical agent Pdx-1 activator(s); chemical agent GK activator (s)+chemical agent PTP1B inhibitor(s)+chemical agent Pdx-1 activator(s)+PTP1B gene; GK gene+chemical agent GK activator(s)+chemical agent PTP1B inhibitor(s)+chemical agent Pdx-1 activator (s); GK gene+chemical agent GK activator(s)+chemical agent PTP1B inhibitor(s)+PTP1B gene; GK gene+chemical agent GK activator(s)+chemical agent PTP1B inhibitor(s)+Pdx-1 gene; Pdx-1 gene+PTP1B gene; Pdx-1 gene+chemical agent PTP1B inhibitor(s); chemical agent Pdx-1 activator(s)+PTP1B gene; chemical agent GK activator(s)+Pdx-1 gene+chemical agent PTP1B inhibitor(s); chemical agent Pdx-1 activator(s)+Pdx-1 gene+PTP1B gene; chemical agent Pdx-1 activator(s)+Pdx-1 gene+chemical agent PTP1B inhibitor(s); PTP1B gene+chemical agent GK activator(s)+chemical agent Pdx-1 activator(s); chemical agent PTP1B inhibitor(s)+Pdx-1 gene+GK gene; chemical agent PTP1B inhibitor(s)+Pdx-1 gene+PTP1B gene; chemical agent PTP1B inhibitor(s)+chemical agent Pdx-1 activator(s)+GK gene; chemical agent PTP1B inhibitor(s)+chemical agent Pdx-1 activator(s)+PTP1B gene; chemical agent PTP1B inhibitor(s)+chemical agent GK activator(s)+PTP1B gene; GK gene+chemical agent GK activator(s)+Pdx-1 gene+chemical agent PTP1B inhibitor(s); chemical agent GK activator(s)+Pdx-1 gene+chemical agent PTP1B inhibitor(s)+PTP1B gene; GK gene+Pdx-1 gene+chemical agent Pdx-1 activator(s)+PTP1B gene; GK gene+Pdx-1 gene+chemical agent Pdx-1 activator(s)+chemical agent PTP1B inhibitor(s); GK gene+chemical agent Pdx-1 activator(s)+PTP1B gene+chemical agent PTP1B inhibitor(s); GK gene+chemical agent GK activator(s)+Pdx-1 gene+chemical agent Pdx-1 activator(s)+PTP1B gene; GK gene+chemical agent GK activator(s)+Pdx-1 gene+chemical agent Pdx-1 activator(s)+chemical agent PTP1B inhibitor(s); GK gene+Pdx-1 gene+chemical agent Pdx-1 activator(s)+PTP1B gene+chemical agent PTP1B inhibitor(s); Pdx-1 gene+chemical agent Pdx-1 activator(s)+PTP1B gene+chemical agent PTP1B inhibitor(s); or Pdx-1 gene+PTP1B gene+chemical agent PTP1B inhibitor(s)+GK gene.

In certain embodiments, a single agent can (i) positively modulate glucokinase activity, and positively modulate tyrosine kinase receptor activity and/or tyrosine kinase associated receptor activity; (ii) positively modulate glucokinase activity, and positively modulate beta cell specific transcription; or (iii) positively modulate tyrosine kinase receptor activity and/or tyrosine kinase associated receptor activity (e.g., inhibit PTB1B), and positively modulate beta cell specific transcription.

In certain aspect chemical agent GK activator(s) can act at two levels increasing the glucose metabolism rate and increasing the Pdx-1 mediated gene expression. Chemical agent PTB1B inhibitor(s) in combination with chemical agent GK activator(s) can target each of the three pathways described herein.

In certain aspects, in disease states such as type II diabetes chemical agent PTP1B inhibitor(s) can act on both the tyrosine kinase receptor level and GK levels in the presence of insulin. In certain aspects a GK activator(s) can increase glucose metabolism and Pdx-1 mediated transcriptional activation. For example, Rosiglitazone increases the expression of GK and Pdx-1 mediated effects. Chemical agent PTP1B inhibitor(s) in combination with insulin secretion competence can increase glucose metabolism and increase tyrosine kinase receptor activity. Furthermore, the family of PPAR-gamma activator(s) like Rosiglitazone increases GK expression and Pdx-1 expression. Thus, a single agent can be administered to modulate multiple target pathways.

As used herein "target cell" and "target cells" refer to precursor cells, isolated cells, stem cells, cells of the pancreas or other organs or tissues that can be induced to form beta cells or beta cell-like cells. The cells can be beta cells or non-beta cells prior to inducement. A precursor cell is a cell that is not fully differentiated.

As used herein, expression refers to mRNA levels (nucleic acid expression) and/or protein levels (protein expression). Oligonucleotides suitable to detect mRNA, e.g., using RT-PCR, can be designed using techniques routine in the art. Alternatively or in addition, protein expression can be assessed using any art-recognized technique (e.g., any antibody based detection technique).

As used herein, the term "treatment," when used in the context of a therapeutic strategy to treat a disease or disorder means any manner in which one or more of the symptoms of a disease or disorder are ameliorated or otherwise beneficially altered. As used herein, amelioration of the symptoms of a particular disease or disorder refers to any lessening, whether permanent or temporary, lasting or transient that can be attributed to or associated with treatment by the compositions and methods of the present invention.

The terms "effective amount" and "effective to treat," as used herein, refer to an amount or a concentration of one or more compounds or a pharmaceutical composition described herein utilized for a period of time (including in vivo acute or chronic administration, and periodic or continuous administration) that is effective within the context of its administration for causing an intended effect or physiological outcome.

Effective amounts of one or more compounds, or a pharmaceutical composition for use in the present invention include amounts that promote beta cell formation or maturity, e.g., an increase in glucose-dependent insulin secreting cells or an increase in glucose-dependent secretion from a cell.

The term "subject" is used throughout the specification to describe an animal, human or non-human, to whom treatment according to the methods of the present invention is provided. In certain aspects, the subject is human.

The term "providing" is used according to its ordinary meaning "to supply or furnish for use." In some embodiments, a protein is provided directly by administering the protein, while in other embodiments, the protein is provided by administering a nucleic acid that encodes the protein. In other embodiments, an inhibitor such as an shRNA can be provided to reduce protein levels in a cell. In certain aspects the invention contemplates compositions comprising various combinations of therapeutic nucleic acids, peptides, and/or small molecules.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification presented herein.

DESCRIPTION

Figure 1:
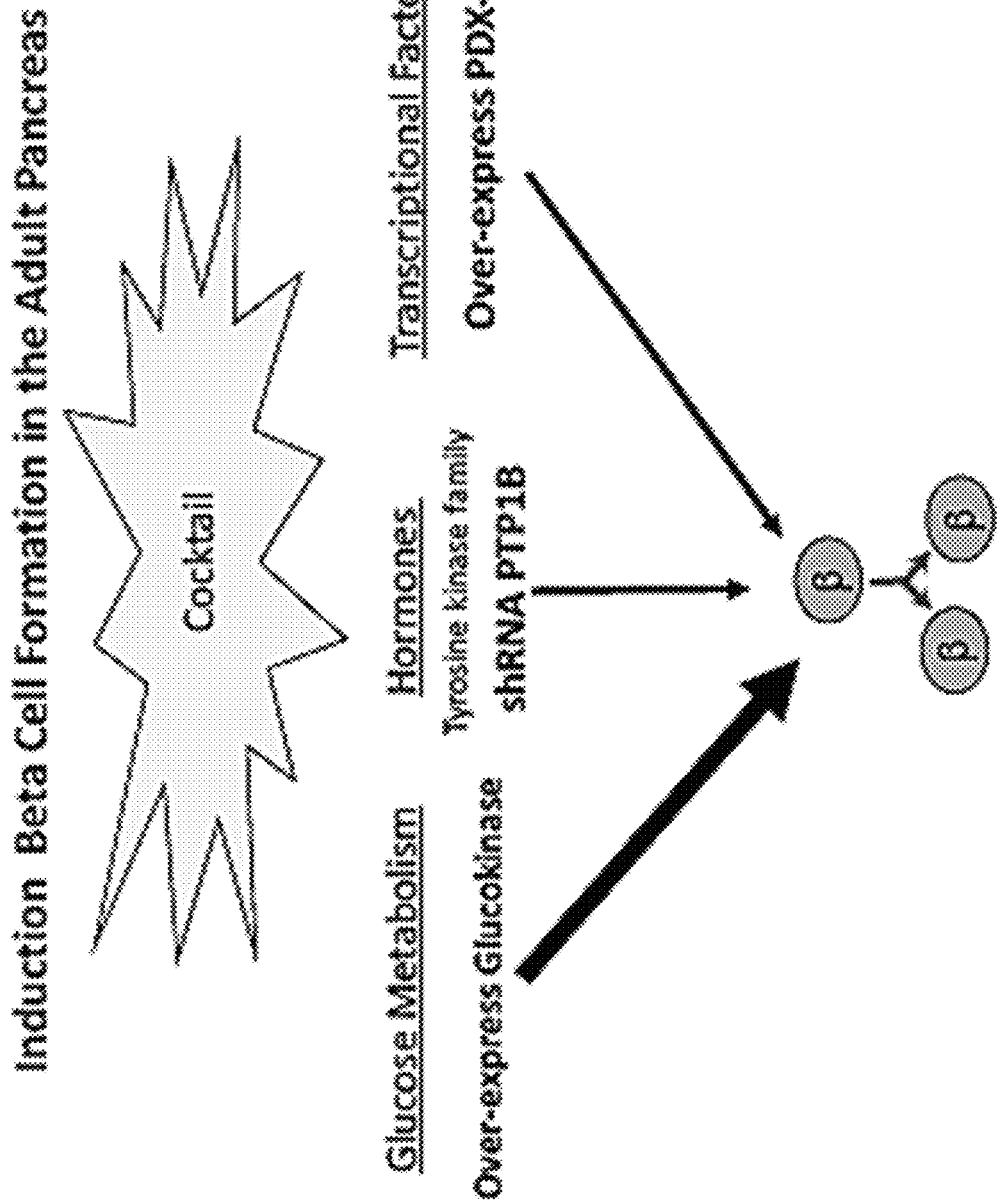
FIG. 1. An example of an approach using an induction cocktail comprising three molecules to induce pancreatic beta cells formation in vivo in the adult pancreas.

Certain methods described herein represent a concept that contradicts the scientific doctrine of one molecule to one cellular control process. In certain aspects, the methods include the integration of three levels of cellular physiology: metabolism, membrane receptor function, and gene transcription. The integration of multiple levels of cellular physiology produces a synergistic effect on beta cell formation. Synergy requires that multiple molecules work together to produce an effect that is greater than the sum of their individual effects. Using the synergistic approach described herein, the inventors have successfully induced pancreatic beta cell formation in the adult pancreas. The ability to generate beta cells in vivo in adult animals and humans provides a novel therapeutic approach for the treatment of subjects with type 1 and type 2 diabetes mellitus.

I. METHODS OF TREATING DIABETES

The inventors have demonstrated that, utilizing "Cellular Networking Integration & Processing" (CNIP), pancreatic beta cell formation can be increased in vivo in adult subjects. According to the CNIP approach, the inventors intervene at three major levels in cell processing: (1) first, at the level of intracellular carbohydrate metabolism, (2) second, at the level of the membrane receptor function, (3) third, at the level of gene expression. By targeting all three levels, one can generate a synergistic interaction that induces beta cell formation. The inventors refer to one example of this method as "Syner-III," with Syner being the prefix from the Greek name synergos and III is Roman number three.

The CNIP approach is designed to mimic the formation of beta cells in adult subjects and not to reprogram the cell at the stage of embryonic development. The inventors note that the cocktail of transcriptional factors used in stem cell research or in the viral vector cocktail used more recently in the mouse model (Zhou et al., Nature 455: 627-32, 2008) are used to generate beta cells by reproducing the embryonic stage of development. In contrast, the CNIP approach is designed to act in the adult state and utilizes a mechanism that integrates the three levels of cellular regulation to induce beta cell formation.

The methods described herein induce pancreatic beta cell formation in vivo in adult subjects without dedifferentiating cells to recapitulate the embryonic pathway. The CNIP approach specifically targets the post-embryonic induction of pancreatic beta cell formation without reproducing the embryonic formation process of the pancreas—the embryonic formation process leads to the generation of multiple pancreatic endocrine cell types. The ability to generate new beta cells in vivo in adult subjects can provide a novel therapeutic approach for the treatment of patients with type 1 and 2 diabetes mellitus, as well as other types of diabetes. The ability to increase the number of pancreatic beta cells in adult subjects can be therapeutic, prophylactic, and/or curative in regards to diabetes.

In certain embodiments, compositions and methods described herein can be applied to tissues other than the pancreas. In certain aspects, compositions described herein can be delivered into the gut endocrine K cells and be an able to form insulin-like beta cell that would secrete insulin in response to an elevation of blood glucose. In a further aspect, the compositions described herein can be delivered to the liver to induce formation of beta cells that respond to glucose. In still other aspects, the compositions described herein can be applied at the last step of stem cell differentiation and/or dedifferentiation to form beta cells. In certain aspects, the compositions described herein can be delivered to various cells and/or tissues in the body to form beta cells and therefore, are not limited to the specific examples described herein.

In certain embodiments target cells are treated in vitro. Target cells are those cells that have the capability or can be induced to have the capability of forming beta cells. Methods for providing or obtaining such target cells are known in the art and include either providing tissue containing target cells and isolating the target cells by methods known in the art, e.g. with the help of cell surface specific antibodies and using a FACS (cell sorter) or cultivation of the cells under specific conditions allowing the growth of target cells. In certain aspects there are suitable target cell lines (Lieber et al., Int J Cancer 15(5):741-47, 1975).

Any cell being capable of differentiating into pancreatic beta cells can be used as a target cell of the method of the invention. This includes precursor cells derived from human or animal (e.g., mammal) tissue. In certain embodiments the target cell is an autologous target cell, i.e., it contains the same genetic information as cells of the subject being treated. In certain aspects the target cell has not been genetically modified prior to the treatment being administered. In certain aspects a target cell is selected from the group consisting of a pancreatic precursor cell, a small intestine precursor cell, a liver precursor cell, a precursor cell derived from the pancreatic duct population, precursor of neuroendocrine cell, and a pancreatic stem cell. This includes all somatic differentiated cells from a human or animal tissue. In certain aspects a target cell is selected from the group consisting of somatic differentiated cell from the liver, endocrine gut cell, pancreatic duct cell, exocrine and endocrine pancreatic cell, and neuroendocrine cell Once target cells have been obtained or provided, the cells can be grown and manipulated in an in vitro cell culture system, which includes standard cell culture systems like tissue culture dishes and 6-well, 24-well or 96-well plates. Culture conditions will depend on the target cell and the person skilled in the art will know how to cultivate the cells.

A. Glucose Metabolism

Glucose metabolism is the first aspect in the CNIP approach to inducing beta cell formation in the adult pancreas or other organs or tissues. Glucose is the major energy source utilized by the mammalian cell, and metabolism of glucose provides the energy for cellular function and proliferation (Bohnsack and Hirschi, Annu Rev Nutr. 24: 433-

453, 2004). Inhibition of glycolysis stops cell cycle progression, documenting the necessity of glucose metabolism to induce proliferation (Newcomb et al., *Eukaryot. Cell.* 2:143-149, 2003). Factors that induce pancreatic beta cell formation in vivo include an increase in glucose metabolism (Bernard et al., *FASEB J.* 13:1195-1205, 1999; Alonso et al., *Diabetes* 56:1792-1801, 2007). Glucose infusion in adult rats for a period of only 24 h increased beta cell number by ~50% (Bernard et al., *FASEB J.* 13:1195-1205, 1999). Furthermore, glucose promotes beta cell survival by suppressing a constitutive apoptotic program in vitro (Hoorens et al., *J. Clin. Invest.* 98:1568-1574, 1996). Glucose metabolism primes the pancreas for induction of pancreatic beta cell formation.

In certain aspects, the rate of glucose metabolism is increased by providing a nucleic acid encoding glucokinase, or increasing the activity of glucokinase or other enzymes or regulators. In certain embodiments the functions ascribed to the nucleic acid described herein can be provide by administering various chemical compounds or small molecules that increase glucose metabolism. Glucokinase activating compounds include, but are not limited to Roche Inc., compound R1440; Hoffman-La Roche Inc., compound RO0281675; Hoffman-La Roche Inc., compound RO4389620 (Piragliatin); Eli Lilly Inc., compound LY2121260; OSI Pharmaceuticals, Inc., compound PSN-GK1; Astra-Zeneca, Inc., compound GKA-50; Pfizer Inc., glucokinase activators described in International Patent publication WO/2007122482); Merck-Banyu Inc., glucokinase activators described in International Patent publication WO/2003080585; Takeda Inc., glucokinase activators described in International Patent publication WO/200710434); Johnson & Johnson Inc., glucokinase activator described in International Patent publication WO/2007075847); and the like.

B. Receptor Tyrosine Kinases and Tyrosine-Kinase-Associated Receptors.

Membrane receptor tyrosine kinase(s) and/or tyrosine-kinase-associated receptors are a second component of the CNIP approach to induce the formation of pancreatic beta cells in an adult subject. The second aspect in the generation of pancreatic beta cells following a physiological stimulus is for the cell to receive the message through its membrane receptors. The membrane receptors responsible for the stimulation of pancreatic beta cell mass are from the tyrosine kinase family of receptors and tyrosine-kinase-associated family of receptors. During pregnancy the pancreatic beta cell mass increases in response to the development of insulin resistance and increased fetal/placenta energy demand and this effect is mediated by increased prolactin, estrogen, and placental lactogen secretion (Heit et al., *Annu. Rev Cell Dev. Biol.* 22:311-338, 2006). The failure of the beta cell to compensate by augmenting its secretion of insulin leads to gestational diabetes. Islet enlargement and beta cell hyperplasia have been observed in autopsied pregnant humans (Van Assche et al., *Br. J. Obstet Gynaecol* 85: 818-820, 1978). The hormonal stimuli (prolactin, estrogen, and placental lactogen) during pregnancy to increase the pancreatic beta cell mass act through tyrosine kinase associated receptors (Nielsen et al., *Diabetes* 50 (Suppl. 1): S25-S29, 2001). Other hormones that increase beta cell mass also act through the tyrosine kinase family of receptors and include hepatocyte growth factor, platelet-derived growth factor, growth hormone, insulin, IGF-1 and EGF (Nielsen et al., *Diabetes* 50 (Suppl. 1): S25-S29, 2001). Of note, the effect of these hormones on beta cell mass also relies on glucose metabolism. In the absence of glucose, the ability of hormones acting through the tyrosine kinase family to increase pancreatic beta cells mass is lost (Cousin et al., *Biochem. J.* 344:649-658, 1999). Consequently, the CNIP approach combines the effect of glucose metabolism, and membrane tyrosine kinase(s) and/or tyrosine-kinase(s) associated receptors to induce beta cell formation in the adult pancreas.

In certain embodiments the function(s) ascribed to the nucleic acids described herein can be provided by administering various chemical compounds or small molecules that increase tyrosine kinase receptor and/or tyrosine-kinase(s) associated receptor activity for beta cell formation in an adult pancreas. In certain aspects, inhibitory nucleic acids such as anti-sense DNA or inhibitory RNA molecules can be used. Such compounds include, but are not limited to PTP1B inhibitor compounds such as Wyeth Research Inc., 32D; antisense ISIS-PTP1BRX; Abbott Laboratories, Inc., Isoxazole; Abbott Laboratories, Inc., antisense oligonucleotides designed to downregulate expression of PTP1B; Merck Frosst Center for Therapeutic Research, selective inhibitors of PTP1B compound 1 and 3; Incyte Corporation, Inc., (S)-isothiazolidinone ((S)-IZD) heterocyclic phosphotyrosine; Affymax, Inc., triaryl sulfonamide based PTP1B inhibitors; and the like.

Other shRNA targeting tyrosine phosphatase family proteins can be included alone or in combination with shRNA PTP1B. PTP1B acts on the majority of the tyrosine kinase family of receptors that have been implicated in pancreatic beta cell function in the adult pancreas. However, T-cell protein tyrosine phosphatase (TCPTP) and SHP-2, two other members of intracellular protein phosphatase, have been shown to target receptor tyrosine kinases implicated insulin signaling (Tonks, *Nat Rev. Mol Cell Biol* 7:833-46, 2006). SHP-2 (SH2-domain containing phosphatase-2) is a ubiquitously expressed intracellular protein tyrosine phosphatase that contains two amino-terminal Src homology 2 (SH2) domains. SH2-2 binds to both the tyrosine-phosphorylated insulin receptor and IRS-1. TCPTP exists in two forms: an endoplasmic reticulum-targeted 48-kDa from (TC48) and a nuclear 45-kDa form (TC45). TC-PTP has been demonstrated to negatively regulate insulin signaling and the prolactin receptor (Aoki and Matsuda, *J. Biol. Chem.* 275: 39718-26, 2000; Tonks, *Nat Rev. Mol Cell Biol* 7:833-46, 2006). Therefore, nucleic acids expressing shRNA-SHP-2 and shRNA-TC-PTP can be used in the methods and compositions described herein.

C. Beta Cell Specific Transcription

The third aspect in the CNIP approach is directed at the level of gene expression and involves a transcriptional activator or transcription factor, which is utilized as an attractor to converge and focus the glucose metabolism effect and metabolic/molecular effects generated by glucokinase, and the tyrosine kinase receptor(s) and tyrosine kinase associated receptor(s) to form beta cells in the adult pancreas. The term "transcription" refers to the process of copying a DNA sequence of a gene into an RNA product, generally conducted by a DNA-directed RNA polymerase using the DNA as a template. Every system has a modulator attractor, like in physics. In a chaotic system, the direction of the network endpoint will follow the force of the attractor. From a simplistic view, the impact target of a projectile will depend on the initial force of propulsion combined with air resistance and the effect of gravity on the projectile. The initial forces, air resistance and gravity, will act in synergy as an attractor to determine the final destination of the projectile. The living organism is a nonlinear dynamic system that exists in a "chaotic" state. At the transcriptional level, the expression of a set of genes remains unchanged and those genes are call "housekeeping" genes. They carry out the routine functions of the cell, whereas other classes of genes are expressed in response to environmental stimuli. In the adaption of pancreatic beta cells to a physiological stress, upregulation of gene expression is essential for the induction of pancreatic beta cell formation (Bouwens and Rooman, *Physiol Rev* 85:1255-1270, 2005). A key mediator of this adaptive response to a physiological stress at the gene expression level involves the activation of modular attractor(s) in the form of transcription factors (Albert and Barabasi, *Rev Mod Physics* 74:47-97, 2002; Albert and Othmer, *J Theor Biol* 223, 1-18, 2003). Therefore, the CNIP approach includes transcription factor(s) (as a modular attractor) that have been implicated in the formation of beta cells in the adult pancreas in response to physiological stress.

Pdx-1 overexpression alone could be used with a synergistic convergence force of other TFs to channel the CNIP gene expression pattern to induce pancreatic beta cell formation. Therefore, other TFs implicated in adult pancreatic beta cell formation and that can increase the effect of Pdx-1 on beta cell formation in vivo can be used in the methods described herein. In certain aspects, TFs implicated in beta cell formation can be used. TFs implicated in other endocrine cell formation can be excluded. The TFs implicated in pancreatic beta cell formation in the post-development period added in combination with or in place of Pdx-1 include: NeuroD, Isl1, Nkx6.1, and Pax4. Anti-diabetic compounds such as anti-diabetic thiazolidinediones (e.g., troglitazone) can also be used in conjunction with TFs to increase beta cell formation. For example, troglitazone increases Pdx-1 expression in mouse islets through the functional peroxisome proliferators-activated receptor gamma (PPARγ) response element in the Pdx-1 promoter (Gupta et al., *J Biol Chem.* 283(47):32462-70, 2008). Also contemplated is the induction of Pdx-1 via positive modulation of the PPARγ response element in the promoter of the Pdx-1 gene.

D. Therapeutic Compositions

In certain aspects, 1, 2, 3, or more of the therapeutic moieties described herein can be combined in one or more composition or administered in combination. In one aspect, one or more therapeutic moiety is provided as a cocktail of 1, 2, 3, or more nucleic delivery vector(s) and/or therapeutic agent(s). Such a cocktail can be administered orally, locally, or systemically as described herein.

In a further aspect, 2, 3, or more of the therapeutic moieties can be joined to create a bi-valent, tri-valent, or tetra-valent composition. Such a composition can be administered orally, locally or systemically as described herein. In certain aspects, such compositions are administered orally. In other aspects the compositions are injected or infused locally.

In still a further aspect, 1, 2, 3, or more therapeutic moieties can be joined in one molecule by chemical adaptor systems. Such a composition can be administered orally, locally or systemically as described herein.

II. NUCLEIC ACID COMPOSITIONS

The term "nucleic acid vector" is used to refer to a carrier nucleic acid molecule into which a nucleic acid sequence can be inserted for introduction into a cell where it can be replicated, transcribed, and/or translated (i.e., expressed). A nucleic acid sequence can be "exogenous," which means that it is foreign to the cell into which the vector is being introduced or that the sequence is "endogenous" to the cell but in a position within the host cell in which the sequence is ordinarily not found. In certain aspects an exogenous vector can encode an endogenous nucleic acid. Nucleic acid vectors include plasmids, cosmids, viral genomes, and other expression vectors (bacteriophage, animal viruses, and plant viruses), artificial chromosomes (e.g., YACs), and the like. Given the current disclosure, one of skill in the art would be well equipped to construct a vector through standard recombinant techniques (see, for example, Maniatis et al., *Molecular Cloning: A laboratory Manual*. Cold Spring Harbor Laboratory, New York, 1989; Ausubel et al., *Current Protocols in Molecular Biology*, New York City, N.Y., John Wiley & Sons, Inc., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of inhibitory RNA, antisense molecules, or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described herein.

Certain aspects involve the use of nucleic acids encoding beta cell inducing components. Examples of nucleic acids include GK as provided in SEQ ID NO: 1 and SEQ ID NO:4; PTB1B shRNA as provided in SEQ ID NO:2; and Pdx-1 as provided in SEQ ID NO:3; or the equivalent as would be recognized by one skilled in the art. In certain aspects the nucleic acid comprise a nucleotide sequence that is 80, 85, 90, 95, 98, or 100% identical to SEQ ID NO: 1, 2, 3, and/or 4. In certain embodiments, nucleic acids of the invention encode proteins that are 80, 85, 90, 95, 98, or 100% identical to the proteins of SEQ ID NO:5 (GK) or SEQ ID NO:6 (Pdx-1) and maintain the appropriate activity.

The sequences may be modified, given the ability of several different codons to encode a single amino acid, while still encoding for the same protein or polypeptide. Optimization of codon selection can also be undertaken in light of the particular organism used for expression.

A. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter generally comprises a sequence that functions to position the start site for RNA synthesis. Additional promoter elements regulate the frequency of transcriptional initiation. Typically, these are located in the region 30-110 by upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the RNA. The spacing between promoter elements frequently is flexible, so that promoter function is preserved when elements are inverted or moved relative to one another. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the nucleic acid under the control of a recombinant, exogenous, or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from another virus, or prokaryotic or eukaryotic cell, and promoters or enhancers not "naturally occurring," i.e., containing different elements of different transcriptional regulatory regions, and/or mutations that alter expression.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al., *Molecular Cloning: A Laboratory Manual*, vol. I. 2nd edition. Cold Spring Harbor Laboratory Press, 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, world-wide-web at epd.isb-sib.ch/) could also be used to drive expression. Use of a T3, T7, or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

In certain aspects, a nucleic acid of the invention can comprise a non-inducible or inducible promoter that will be expressed specifically in the pancreatic tissues. Such non-inducible promoters include tissue-specific pancreas promoters from the insulin gene, glucagon gene, amylase gene, etc. Such inducible promoters include pancreas specific promoters under the control of the glucose response element or pancreas specific promoter under the control of a response element that is inducible by chemical, peptide, ligand, or metabolites.

B. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

C. Multiple Cloning Sites

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that function only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

D. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, the termination sequences such as bovine growth hormone terminator or viral termination sequences, such as the SV40 terminator. In certain embodiments, the termination signal may be a lack of transcribable or translatable sequence, such as due to a sequence truncation.

E. Post-Transcriptional Regulatory Elements (PRE)

Post-transcriptional regulation is the control of gene expression at the RNA level, i.e., between the transcription and the translation of the gene. In certain aspects, the Woodchuck Hepatitis Virus Post-transcriptional Regulatory Element (WPRE) is used. WPRE increases the levels of nuclear transcripts and facilitates RNA export. WPRE may facilitate other steps in RNA processing, directing RNAs that would normally be degraded within the nucleus to be efficiently expressed. The WPRE can also function to facilitate the generation of RNA-protein complexes that would protect newly synthesized transcripts from degradation in the nucleus. (Zufferey et al., *Journal of Virology*, 73: 2886-2892, 1999 and U.S. Pat. No. 6,284,469, which is incorporated herein by reference).

F. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

G. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

H. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with fluorescence assisted cell sorting (FACS) and/or immunohistochemistry. The marker used is not believed to be important, so long as it is capable of being expressed simultaneously with the nucleic acid encoding a gene product. Further examples of selectable and screenable markers are well known to one of skill in the art.

III. POLYPEPTIDE COMPOSITIONS

Modifications and/or changes may be made in the amino acid composition of polypeptides, and thus the present invention contemplates variation in sequences of the polypeptides, and nucleic acids coding therefor, where they are nonetheless able retain substantial activity with respect to the therapeutic, preventative, and curative aspects of the present invention.

The biological functional equivalent may comprise a polynucleotide that has been engineered to contain distinct sequences while at the same time retaining the capacity to encode the "wild-type" or standard peptide. This can be accomplished through the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide may encode a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges on the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or nucleotides) may be substituted. In certain aspects, a polypeptide is 80, 85, 90, 92, 94, 96, 98, or 100% identical to the wildtype form of the polypeptide. In certain aspects, polypeptide(s) 80, 85, 90, 92, 94, 96, 98, or 100% identical to SEQ ID NO: 5 or 6 are used or nucleic acids encoding the same.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification. Function of a polypeptide can be determined by using various assays know to detect the activity of the polypeptide of interest.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine, and/or histidine are all positively charged residues; that alanine, glycine, and/or serine are all a similar size; and/or that phenylalanine, tryptophan, and/or tyrosine all have a generally similar shape. Therefore, based upon these considerations, arginine, lysine, and/or histidine; alanine, glycine, and/or serine; and/or phenylalanine, tryptophan, and/or tyrosine are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within +2 is preferred, those that are within +1 are particularly preferred, and/or those within +0.5 are even more particularly preferred.

It also is understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within +2 is preferred, those that are within +1 are particularly preferred, and/or those within +0.5 are even more particularly preferred.

In certain embodiments recombinant polypeptides as described herein comprise protein transduction domains. Protein transduction domains (PTDs) have the ability to translocate across biological membranes. The PTDs are relatively short (one- to 35-amino acid) sequences that confer this apparent translocation activity to proteins and other macromolecular cargo to which they are conjugated, complexed or fused. The HIV-derived TAT peptide (YGRKKRRQRRR (SEQ ID NO:7)), for example, has been used widely for intracellular delivery of various agents ranging from small molecules to proteins, peptides, range of pharmaceutical nanocarriers and imaging agents. Alternatively, receptor-mediated endocytic mechanisms can also be used for intracellular drug delivery. For example, the transferrin receptor-mediated internalization pathway is an efficient cellular uptake pathway that has been exploited for site-specific delivery of drugs and proteins. This is achieved either chemically by conjugation of transferrin with therapeutic drugs or proteins or genetically by infusion of therapeutic peptides or proteins into the structure of transferrin. Naturally existing proteins (such as the iron-binding protein transferrin) are very useful in this area of drug targeting since these proteins are biodegradable, nontoxic, and non-immunogenic. Protein transduction domains include, but are not limited to, PTDs derived from proteins such as human immunodeficiency virus 1 (HIV-1) TAT (Ruben et al., *J. Virol.* 63:1-8, 1989), e.g., GRKKRRQRRR (TAT 48-57, SEQ ID NO:8); the herpes virus tegument protein VP22 (Elliott and O'Hare Cell 88:223-33, 1997); the homeotic protein of *Drosophila melanogaster* Antennapedia (Antp) protein (Penetratin PTD; Derossi et al. *J. Biol. Chem.* 271:18188-93, 1996); the protegrin 1 (PG-1) anti-microbial peptide SynB (e.g., SynB1, SynB3, and Syn B4; Kokryakov et al. *FEBS Lett.* 327:231-36, 1993); and basic fibroblast growth factor (Jans *FASEB J.* 8:841-47, 1994). PTDs also include synthetic PTDs, such as, but not limited to, polyarginine peptides (Futaki et al., *J. Mol. Recognit.* 16:260-64, 2003; Suzuki et al., *J. Biol. Chem.* 276:5836-40, 2001); transportan (Pooga et al., *FASEB J* 12:67-77, 1988; Pooga et al., *FASEB J.* 15:1451-53, 2001); MAP (Oehlke et al., *Biochim. Biophys. Acta.* 1414:127-39, 1998); KALA (Wyman et al., *Biochemistry* 36:3008-17, 1997); and other cationic peptides, such as, for example, various β-cationic peptides (Akkarawongsa et al., *Antimicrob. Agents and Chemother.* 52(6):2120-29, 2008).

IV. DELIVERY VECTORS

In certain aspects, components are provided to a pancreas or other organ or tissue by using nucleic acids that encode or express such components. Viral and non-viral delivery vectors can be used in the methods described herein (e.g., Syner-III). The term "nucleic acids", "nucleic acid molecules", "nucleic acid sequences", "nucleotide sequences" and "nucleotide molecules" are used interchangeably herein and, unless otherwise specified, refer to a polymer of deoxyribonucleic acids, including cDNA, DNA, PNA, or polymers of ribonucleic acids (RNA). Nucleic acid may be obtained from a cellular extract, genomic or extragenomic DNA, viral nucleic acids, or artificially/chemically synthesized molecules. The term can include double stranded or single stranded deoxyribonucleic or ribonucleic acids.

A. Viral Delivery

The ability of certain viruses to infect cells or enter cells via receptor-mediated endocytosis, and to express virally encoded genes have made them attractive candidates for the transfer of foreign nucleic acids into cells (e.g., mammalian cells). Viruses may thus be utilized that encode and express agents to increase the activity of glucose metabolism, increase tyrosine kinase receptor activity, and increase transcription of genes associated with beta cells. Non-limiting examples of virus vectors that may be used to deliver nucleic acids are described below.

Adenoviral Vectors.

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, *Semin. Virol.* 3, 237-252, 1992).

AAV Vectors.

The nucleic acid may be introduced into the cell using adenovirus-assisted transfection. Increased transfection efficiencies have been reported in cell systems using adenovirus-coupled systems. Adeno-associated virus (AAV) has a low frequency of integration and it can infect non-dividing cells, thus making it useful for delivery of genes into mammalian cells in tissue culture or in vivo. AAV has a broad host range for infectivity. Details concerning the generation and use of rAAV vectors are described in U.S. Pat. Nos. 5,139,941 and 4,797,368, each of which incorporated herein by reference.

Retroviral Vectors.

Retroviruses have the ability to integrate their genes into the host genome, transferring a large amount of foreign genetic material, infecting a broad spectrum of species and cell types and of being packaged in special cell-lines. In order to construct a retroviral vector, a nucleic acid (e.g., one encoding a protein of interest) is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types.

Lentiviruses are complex retroviruses, which, in addition to the common retroviral genes gag, pol, and env, contain other genes with regulatory or structural function. Lentiviral vectors are well known in the art (see, for example, U.S. Pat. Nos. 6,013,516 and 5,994,136, each of which is incorporated herein by reference). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, which is incorporated herein by reference.

One may target the recombinant virus by linkage of an envelope protein with an antibody or a particular ligand for targeting to a receptor of a particular cell-type. By inserting a sequence (including a regulatory region) of interest into the viral vector, along with another gene that encodes the ligand for a receptor on a specific target cell, for example, the vector is now target-specific. Such viral vectors can be targeted to cells of the pancreas.

Other Viral Vectors.

Other viral vectors may be employed in the methods of the present invention. Vectors derived from viruses such as vaccinia virus (Ridgeway, In: *Vectors: A survey of molecular cloning vectors and their uses*, Rodriguez and Denhardt (Eds.), Stoneham: Butterworth, 467-492, 1988; Baichwal and Sugden, In: *Gene Transfer*, Kucherlapati (Ed.), NY, Plenum Press, 117-148, 1986; Coupar et al., *Gene* 68:1-10, 1988), sindbis virus, cytomegalovirus, and herpes simplex virus may be employed. They offer several attractive features for various mammalian cells (Friedmann, *Science*, 244:1275-1281, 1989; Ridgeway, In: *Vectors: A survey of molecular cloning vectors and their uses*, Rodriguez and Denhardt (Eds.), Stoneham: Butterworth, 467-492, 1988; Baichwal and Sugden, In: *Gene Transfer*, Kucherlapati (Ed.), NY, Plenum Press, 117-148, 1986; Coupar et al., *Gene* 68:1-10, 1988; Horwich et al., *J. Virol.* 64:642-650, 1990).

Modified Viruses.

A nucleic acid to be delivered may be housed within an infective virus that has been engineered to express or is coupled to a specific binding ligand. The virus particle will thus bind specifically to the cognate receptors of the target cell and deliver the contents to the cell. A novel approach designed to allow specific targeting of virus vectors was developed based on the chemical or genetic modification of a virus by the chemical addition or recombinant engineering of moieties to or in surface proteins of the virus. One such modification using lactose moieties can permit the specific infection of hepatocytes via sialoglycoprotein receptors.

Another approach to targeting of recombinant viruses was designed in which biotinylated antibodies against a viral surface protein and against a specific cell receptor were used. The antibodies can be coupled via biotin by using streptavidin (Roux et al., *Proc. Natl. Acad. Sci. USA*, 86:9079-83, 1989). Using antibodies against major histocompatibility complex class I and class II antigens, they demonstrated the infection of a variety of human cells that bore those surface antigens with an ecotropic virus in vitro (Roux et al., *Proc. Natl. Acad. Sci. USA*, 86:9079-83, 1989).

In certain aspects, an adaptor system can be used, i.e., a molecule that binds both the delivery vector and a target-pancreatic cell receptor to facilitate transduction in the pancreas. In a further aspect, use of a native viral vector receptor can be fused to the pancreas targeting ligand. In still another aspect, a bispecific antibody, two antibodies coupled together, can be coupled to the delivery vector resulting the delivery vector having specificity for the target pancreatic cells. In certain aspects, a targeting moiety can be bound to the delivery vector by chemical means. In further aspects, an antibody that binds to a genetically incorporated Ig-binding domain of the delivery vector can be used to enhance delivery. In further aspects, small targeting motifs can be inserted into the capsid, envelope, viral attachment, other viral surface protein to target the pancreatic cells.

In certain aspects, a viral construct can encode for two heterologous protein components (e.g., GK and Pdx-1) and express an shRNA PTP1B. In a further aspect, each component can be comprised in individual and separate viruses.

The compositions described herein can be delivered via the pancreatic duct through endoscopy. Briefly, the patient is sedated or anaesthetized, and a flexible endoscope is inserted through the mouth, down the esophagus, into the stomach, through the pylorus into the duodenum where the ampulla of Vater (the opening of the common bile duct and pancreatic duct) exists. The sphincter of Oddi is a muscular valve that controls the opening of the ampulla. The region can be directly visualized with the endoscopic camera while performing the procedure. A plastic catheter or cannula is inserted through the ampulla, and the beta cell inducing composition (e.g., Syner-III) is introduced into the pancreatic bile duct to target the pancreas. The beta cell forming composition can also be delivered intravenously by coupling a viral vector with a pancreas targeting moiety, e.g, modifying the envelop structure of viral vector to target only the pancreatic tissues.

B. Lipid-Mediated Transfection

In a further embodiment, a nucleic acid may be entrapped in a lipid particle such as, for example, a liposome. Liposomes are vesicular structures characterized by a phospho-lipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: *Liver Diseases, Targeted Diagnosis and Therapy Using Specific Receptors and Ligands*, Wu et al. (Eds.), Marcel Dekker, NY, 87-104, 1991). Also contemplated is a nucleic acid complexed with Lipofectamine (Gibco BRL) or Superfect (Qiagen).

Lipid-mediated nucleic acid delivery and expression of foreign DNA in vitro has been very successful (Nicolau and Sene, *Biochim. Biophys. Acta*, 721:185-190, 1982; Fraley et al., *Proc. Nat. Acad. Sci. USA*, 76:3348-3352, 1979; Nicolau et al., *Methods Enzymol.* 149:157-176, 1987). The feasibility of lipid-mediated delivery and expression of foreign DNA in cultured chick embryo, HeLa and hepatoma cells has also been demonstrated (Wong et al., *Gene* 10:87-94 1980).

In certain embodiments of the invention, a lipid particle may be complexed with a hemagglutinating virus (HVJ). This has been shown to facilitate fusion with the cell membrane and promote cell entry of lipid-encapsulated DNA (Kaneda et al., *Science* 243:375-378 1989). In other embodiments, a lipid particle may be complexed or employed in conjunction with nuclear non-histone chromosomal proteins (HMG-1) (Kato et al., *J. Biol. Chem.* 266: 3361-3364, 1991). In yet further embodiments, a lipid particle may be complexed or employed in conjunction with both HVJ and HMG-1. In other embodiments, a delivery vehicle may comprise a ligand and a lipid particle.

In certain aspects, components described herein, including shRNA of PTP1B and nucleic acids encoding Pdx-1 and glucokinase can be delivered by liposomes. Liposomes containing the nucleic acids could be delivered intravenously and liberated when it reaches the pancreatic tissues. In certain aspects, nucleic acids of the invention are incorporated into liposomes that contain chemically coupled ligands that are presented on the liposome surface. The ligands specifically target pancreatic cells. Using this strategy, a variety of ligands or receptors, such as antibodies, growth factors, cytokines, hormones, and toxins, can be anchored on liposome surface so that the beta cell inducing components can be targeted to and introduced into pancreatic cells.

C. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, *J. Biol. Chem.* 262:4429-4432, 1987; EP patent 0273085), which establishes the operability of the technique. In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a lipid particle. The nucleic acid(s) to be delivered are housed within the lipid particle and the specific binding ligand is functionally incorporated into the lipid layer. The lipid particle will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a lipid particle itself, which will preferably comprise one or more lipids or glycoproteins that direct cell-specific binding. For example, lactosyl-ceramide, a galactose-terminal asialganglioside, have been incorporated into lipid particles and observed to increase the uptake of the insulin gene by hepatocytes (Nicolau et al., *Methods Enzymol.* 149:157-176, 1987). It is contemplated that the tissue-specific transforming constructs of the present invention can be specifically delivered into a target cell in a similar manner or as described herein.

D. Microprojectile Bombardment

Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., *Nature* 327, 70-73, 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force. The microprojectiles used have consisted of biologically inert substances such as tungsten or gold particles or beads. Exemplary particles include those comprised of tungsten, platinum, and gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

Naked plasmid DNA can be transferred into a cell by air pistol (Gene Gun). Syner-III plasmid could be injected via the pancreatic duct using the gene gun approach with endoscopy to reach the pancreatic tissues. The plasmid DNA bombardments through a gene gun enter the cell by physical pressure that opens membrane pores and/or by facilitating diffusion of the naked plasmid DNA though the cell membrane.

E. Nanoparticles

Nucleic acids of the invention can be incorporated into three-dimensional, multicomponent structures of nanoparticles that target pancreatic or other tissues. The nanoparticles used include, but are not limited to liposomes, polymers, proteins, micelles, dendimers, quantum dots, nanoshells, nanocrystals, gold nanoparticles, paramagnetic nanoparticles, and carbon nanotubes.

F. Hydrodynamic Gene Delivery

Naked plasmid DNA can be delivered via the pancreatic duct employing hydrodynamic gene delivery. A balloon catheter can be placed in the pancreatic duct. The balloon catheter placed in the pancreatic duct is inflated for occlusion-assisted infusion.

G. Electroporation

In certain aspects, a pair of electrodes can be placed on or in pancreatic or other tissues, and nucleic acids of the invention are deposited on the electrodes so that the genetic material is transferred into the tissues.

H. Ultrasound-Facilitated Gene Transfer

Nucleic acids of the invention can be incorporated into microbubbles that are injected intravenously. When the microbubbles reach the pancreas or other tissue they are targeted with ultrasound. As the micorbubbles expand and burst, they release the nucleic acids in the pancreas. The local shock waves cause nucleic acids to permeate the nearby cell membranes.

I. Gene Transfer by Needle

In certain aspects, nucleic acids of the invention are injected directly into the pancreas or other tissue using a needle.

V. PHARMACEUTICAL COMPOSITIONS

In light of the current specification, the determination of an appropriate treatment regimen (e.g., dosage, frequency of administration, systemic vs. local, etc.) is within the skill of the art. For administration, the components described herein will be formulated in a unit dosage form (solution, suspension, emulsion, etc.) in association with a pharmaceutically acceptable carrier. Such vehicles are usually nontoxic and non-therapeutic. Examples of such vehicles are water, saline, Ringer's solution, dextrose solution, and Hank's solution. Non-aqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives.

The therapeutic compositions described herein, as well as their biological equivalents, can be administered independently or in combination by any suitable route. Examples of parenteral administration include intravenous, intraarterial, intramuscular, intraperitoneal, and the like. The routes of administration described herein are merely an example and in no way limiting.

The dose of the therapeutic compositions administered to an animal, particularly in a human, in accordance with embodiments of the invention, should be sufficient to result in a desired response in the subject over a reasonable time frame. It is known that the dosage of therapeutic compositions depends upon a variety of factors, including the strength of the particular therapeutic composition employed, the age, species, condition or disease state, and the body weight of the animal.

Moreover, dose and dosage regimen, will depend mainly on the type of biological damage to the host, the type of subject, the history of the subject, and the type of therapeutic composition being administered. The size of the dose will be determined by the route, timing and frequency of administration as well as the existence, nature and extent of any adverse side effects that might accompany the administration of a particular therapeutic composition and the desired physiological effect. It is also known that various conditions or disease states, in particular, chronic conditions or disease states, may require prolonged treatment involving multiple administrations.

Therefore, the amount of the therapeutic composition must be effective to achieve an enhanced therapeutic index. If multiple doses are employed, the frequency of administration will depend, for example, on the type of subject. One skilled in the art can ascertain upon routine experimentation the appropriate route and frequency of administration in a given subject that are most effective in any particular case. Suitable doses and dosage regimens can be determined by conventionally known range-finding techniques. Generally, treatment is initiated with smaller dosages, which are less than the optimal dose of the compound. Thereafter, the dosage is increased by small increments until the optimal effect under the circumstances is obtained.

The therapeutic compositions for use in embodiments of the invention generally include carriers. These carriers may be any of those conventionally used and are limited only by the route of administration and chemical and physical considerations, such as solubility and reactivity with the therapeutic agent. In addition, the therapeutic composition may be formulated as polymeric compositions, inclusion complexes, such as cyclodextrin inclusion complexes, liposomes, microspheres, microcapsules, and the like, without limitation.

The pharmaceutically acceptable excipients described herein, for example, vehicles, adjuvants, carriers, or diluents, are well known and readily available. It is preferred that the pharmaceutically acceptable carrier be one which is chemically inert with respect to the therapeutic composition and one that has no detrimental side effects or toxicity under the conditions of use.

The choice of excipient will be determined, in part, by the particular therapeutic composition, as well as by the particular method used to administer the composition. Accordingly, there are a wide variety of suitable formulations of the pharmaceutical composition used in the embodiments of the invention. For example, the non-limiting formulations can be injectable formulations such as, but not limited to, those for intravenous, subcutaneous, intramuscular, intraperitoneal injection, and the like, and oral formulations such as, but not limited to, liquid solutions, including suspensions and emulsions, capsules, sachets, tablets, lozenges, and the like. Non-limiting formulations suitable for parenteral administration include aqueous and non-aqueous isotonic sterile injection solutions, including non-active ingredients such as antioxidants, buffers, bacteriostats, solubilizers, thickening agents, stabilizers, preservatives, surfactants, and the like. The solutions can include oils, fatty acids, including detergents and the like, as well as other well known and common ingredients in such compositions, without limitation.

VI. EXAMPLES

The following examples as well as the figures are included to demonstrate certain embodiments of the invention. It should be appreciated by those of skill in the art that the techniques disclosed in the examples or figures represent techniques discovered by the inventors to function well in the practice of the described methods, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention.

Example 1

Beta Cell Formation in Adult Pancreas

A. Results

For illustration purposes, the therapeutic moieties include Lentivirus-CMV-Glucokinase (GK), Lentivirus-H1-shRNA PTP1B; and Lentivirus-CMV-PDX-1. The control composition includes Lentivirus-CMV-GFP and Lentivirus-H1-shRNA Scramble injected at the same concentration as the therapeutic composition. Four-weeks post-injection in vivo over-expression of PDX-1 and GK, and suppression of PTP1B expression was detected in the mouse pancreas. Glucokinase over-expression was detected in the islets and in exocrine tissues. Expression of glucokinase in the exocrine tissues confirms the over-expression of the glucokinase by the therapeutic composition since pancreatic tissues only express glucokinase in endocrine cells. Pdx-1 over expression is detected by using a c-Myc tag incorporated into the cDNA of Pdx-1 to differentiate between exogenous and endogenous expression. shRNA PTP1B co-expressing GFP was also detected. Protein expression was confirmed by western blot.

First Aspect of CNIP Approach:

One goal of the CNIP approach is to increase glucose metabolism in the pancreas to induce pancreatic beta cell formation. For glucose to enter the glycolytic pathway, it first must enter the intracellular space through a membrane glucose transport system. The glucose transporters, Glut 1 and Glut 3, are present in exocrine and endocrine human pancreatic tissues, and Glut 2 is present in the pancreatic beta cell (Coppieters et al., *Diabetes Metab Res Rev* 27: 746-754, 2011). However, glucose transport is not the rate-limiting step for glucose entry into the glycolytic pathway (Wasserman et al., *J. Exp. Biol.* 214:254-262, 2011). The first rate-limiting step for glucose metabolism in the glycolytic pathway is at the level of glucose phosphorylation by hexokinase. The phosphorylation of glucose by hexokinase produces the metabolite glucose 6-phosphate (G-6-P). The pancreatic beta cells contain a hexokinase type IV, named glucokinase (GK). Glucokinase is not allosterically inhibited by the accumulation of intracellular G-6-P, in contrast to other hexokinases. Therefore, for glucokinase, the amount and activity of the glucokinase enzyme regulates the rate of glucose flux through glycolysis. For other members of the hexokinase family, product inhibition by G-6-P is the key regulator of enzyme activity and, therefore, glucose entry into the glycolytic pathway. If glucose is not phosphorylated by hexokinase, it cannot undergo further metabolism and cannot generate any signal to the transcriptional machinery to induce gene expression (Doiron et al., *J Biol Chem.* 269: 10213-10216, 1994 and *J Biol Chem.* 271:5321-5324, 1996). Therefore, in certain aspects glucokinase can be included in a CNIP cocktail to induce pancreatic beta cell formation.

Figure 2:
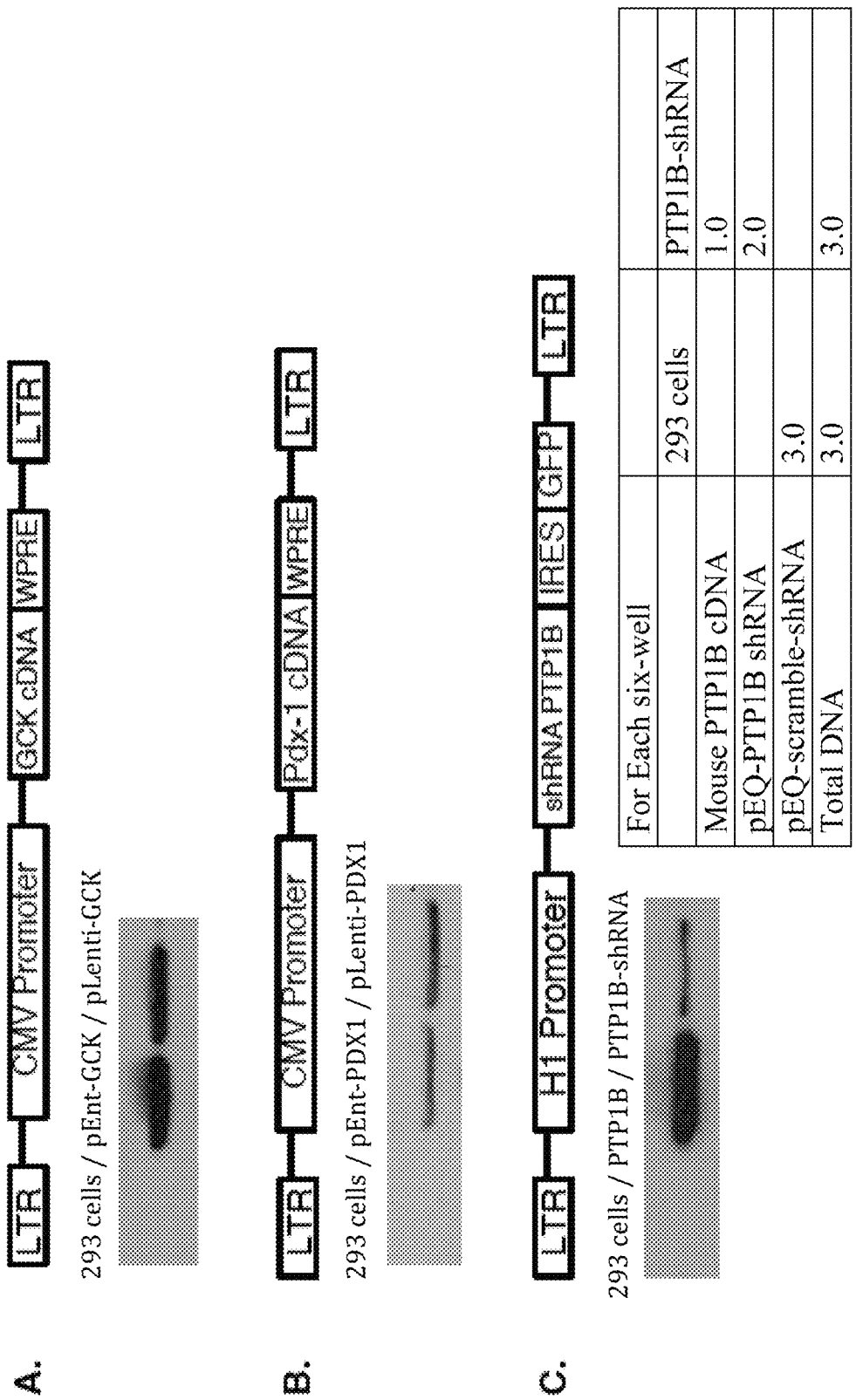
FIG. 2. Illustrates the design and validation of Lentiviral constructs, (A) glucokinase, (B) Pdx-1, and (C) shRNA PTP1B.

The inventors designed a lentiviral vector construct expressing the glucokinase gene under control of the cytomegalovirus (CMV) promoter (FIG. 2, A). The lentiviral vector construct included a posttranscriptional regulatory element of woodchuck hepatitis virus (WPRE) at the 3' untranslated region of coding sequence, which increased the level of expression of the transgene. WPRE functions within the nucleus to stimulate gene expression posttranscriptionally by increasing the levels of nuclear transcripts and greatly increasing the RNA half-life (Zufferrey et al., *J. Virol.* 73:2886-289, 1999). The mouse glucokinase (GCK) gene was subcloned to pEntCMV-WPRE vector and the insert was verified by DNA sequencing. The pENT-GCK was treated with LR Clonase II enzyme (Invitrogen) and ligated to a pLenti vector. The recombination product was transformed into *E. coli* cells. After overnight incubation, the positive clones were selected, and plasmid DNA was purified. The pEnt-GCK and pLenti-GCK were transfected into 293 cells. 48 hours after transfection, the cells were lysed in SDS-PAGE buffer and subjected to 4-20% SDS-PAGE gel electrophoresis and analyzed by Western blotting. The Western blot was carried out using the anti-GCK antibody at a 1:1000 dilution, followed by a HRP conjugated secondary antibody. The Western blot membrane was developed using ECL reagents.

The pLenti-GCK is used for the production of pure, high titer lentiviral vector. The Lenti-GCK will be injected directly into the pancreas of adult mice as described above. Adult mice C57BL/6 (8 weeks old; from Charles River, Wilmington, Mass.) will be used for the in vivo experiment targeting the pancreas with lentiviral vector construct.

Increased glucokinase expression with a plasmid vector has been shown to increase the glucose-6-phosphate (G-6-P) pool (Doiron et al., *J Biol Chem.* 269: 10213-10216, 1994). Glucose 6-phosphate is a key intermediate that sits at the junction of several metabolic pathways (glycolysis, gluconeogenesis, pentose phosphate pathway, glycogenesis and glycogenolysis). Doiron et al (1996) demonstrated that the glucose signal to the transcriptional machinery is mediated by xylulose 5-phosphate, which is a metabolite produced by the pentose phosphate pathway. As demonstrated by Doiron, xylulose 5-phosphate is the major metabolite responsible for mediating transcriptional machinery induction by glucose metabolism. The key enzyme that regulates metabolic flux through the pentose phosphate pathway is glucose-6-phosphate dehydrogenase (G6PD). G-6-P enters the pentose phosphate pathway through the action of G6PD enzyme. Therefore, in the development of our CNIP approach, the combination of Lenti-CGK and Lenti-G6PD to channel glucose 6-phosphate into the pentose phosphate pathway to enhance xylulose-5-phosphate formation that mediates the transcriptional effects of glucose metabolism can be used. Another important enzyme in the formation of xylulose 5-phosphate is transketolase (TK), which is located further down the pentose phosphate pathway. Therefore, an alternative approach will be to combine Lenti-TK with Lenti-CGK to increase the effect of glucose metabolism regulated gene expression. The synergistic action of all molecules (Lenti-CGK, Lenti-G6PD and Lenti-TK) can be used to activate the transcriptional machinery under the control of glucose metabolism and increase beta cell formation.

Second Aspect of CNIP Approach:

The second aspect of the CNIP approach includes increasing membrane receptor tyrosine kinase activity and tyrosine kinase associated receptor activity. Glucose metabolism is a major mechanism involved in the formation of beta cells in the adult pancreas. Another system implicated in beta cell formation is ligand binding to tyrosine kinase receptor(s). (Vasavada et al., *Int J Biochem Cell Biol.* 38:931-950, 2006). The increase in pancreatic beta cell mass in response to physiological stress (i.e. pregnancy) is mediated by growth hormone, prolactin, and placental lactogen working through the prolactin receptor. The prolactin receptor does not have intrinsic tyrosine kinase activity but it interacts with members of the Janus kinase family of tyrosine kinases. Prolactin receptor is part of the family of tyrosine kinase associated receptor(s). The Janus kinase family of tyrosine kinases is responsible for the increase in beta cell mass in response to hormonal changes that occur in pregnancy (Vasavada et al., *Int J Biochem Cell Biol.* 38:931-950, 2006). The action of insulin, insulin-like growth factors, hepatocyte growth factor, and epidermal growth factor also increase beta cell mass by activating a membrane bound tyrosine kinase receptor (Vasavada et al., *Int J Biochem Cell Biol.* 38:931-950, 2006). Therefore, lactogens (including growth hormone, prolactin and placental lactogen), insulin, insulin-like factors, hepatocyte growth factor and epidermal growth factor receptor require the activation of tyrosine kinase(s) to increase pancreatic beta cells mass.

Protein-tyrosine phosphatase 1B (PTP1B) has been shown to inhibit the ability of insulin, insulin-like growth factors receptor, prolactin and hepatocyte growth factor to activate tyrosine kinase(s) (Aoki and Matsuda, *J. Biol. Chem.* 275:39718-39726, 2000; Kakazu et al., *Invest Opthalmol Vis Sci.* 49:2927-2935, 2008; Tonks, *Nat Rev. Mol Cell Biol* 7:833-46, 2006). Consequently, one molecule that can be included in a CNIP cocktail is an inhibitor or inhibitory RNA (e.g., shRNA) targeting PTP1B. The suppression of PTP1B protein production by shRNA will increase receptor tyrosine kinase activity involved in beta cell formation in the adult pancreas in response to binding of a physiological concentration of the corresponding hormone. The shRNA PTP1B has been introduced into a lentivirus construct using the same method described above for lenti-CGK under the control of the H1 polymerase promoter (Doiron et al., *Diabetologia* 55:719-728, 2012) (FIG. 2, C). The polymerase III promoter H1 is active ubiquitously in all cells, because of the housekeeping function of polymerase III. The lenti-shRNA-PTP1B was provided to the pancreas as described above.

Lentivirus shRNA PTP1B. A small hairpin RNAi was constructed into pEQU6 vector. The target sequences are 20 nt in length (GCCAGGACATTCGACATGAA SEQ ID NO:2). The shRNAi sequences were verified by DNA sequencing.

Co-transfection experiments were performed using the target gene expression plasmid pEnt-PTP1B and one pEQ-PTP1B-shRNA vector. The chart below describes the component of each reaction. 48 hours after transfection, cells were lysed in SDS-PAGE buffer and subjected to 4-20% SDS-PAGE gel electrophoresis and Western blot analyses. The Western blot was carried out using the anti-PTP1B antibody at a 1:1000 dilution. The membrane was evaluated using ECL reagents. For each 6-well:

|  | 293 cells | PTP1B-shRNA |
| --- | --- | --- |
| mouse PTP1B cDNA |  | 1.0 |
| pEQ-PTP1B shRNA |  | 2.0 |
| pEQ-scramble-shRNA | 3.0 |  |
| Total DNA | 3.0 | 3.0 |

Third Aspect of CNIP Approach:

A third aspect that can be included in the methods described herein includes increasing gene expression through transcriptional factor(s) to integrate the effect of glucose metabolism (Aspect 1) and stimulation of tyrosine kinase receptor family activity (Aspect 2) to induce beta cell formation in the pancreas.

Different models have been proposed to explain the facilitated diffusion of transcriptional factors to bind to their target DNA sequence into the nucleus. One model proposes that the transcriptional factor (TF) binds the DNA by facilitated diffusion. First, the TF interacts with the DNA randomly at a non-specific site. After initial TF interaction with the DNA molecules, by facilitated diffusion, the TF moves from its initial non-specific site to its target sequence by 'sliding' along the DNA. As the TF rolls along the DNA and finds its corresponding binding site, it induces activation or inhibition of the transcriptional machinery. Irrespective of the model proposed to explain how the TF reaches its DNA binding site, all proposed models and experiments include facilitated diffusion with random movement of the TF to find its site of activation or inhibition in the transcriptional machinery. One action of glucose metabolism signaling to the transcriptional machinery is to increase the probability of the TF binding the DNA molecule (Doiron et al., *J Biol Chem.* 271:5321-5324, 1996). Indeed, glucose metabolism signaling to the transcriptional machinery induces TF expression and TF translocation from the cytoplasm to the nucleus turns on glucose-induced genes (Doiron et al., *J Biol Chem.* 271:5321-5324, 1996). Consequently, the biophysical mechanism by which TFs increase glucose-induced gene expression depends on the TF quantity level present in the nucleus. Indeed, when the quantity of TFs in the nucleus increases, the chances of interacting with DNA molecules to randomly find its specific binding site increased (Mitanchez et al., *Endo Rev* 18:520-540, 1997). Increasing expression of genes implicated in beta cell formation in the adult pancreas can be accomplished or enhanced by overexpressing key TFs that activate the beta cell formation pathway.

One of the major transcriptional factors implicated in beta cell formation after birth is Pdx-1 (Doiron and DeFronzo, *Int J Endocrinol Metab.* 9:356-357, 2011). Pdx-1 has distinct effects before and after birth in the pancreas (Doiron and DeFronzo, *Int J Endocrinol Metab.* 9:356-357, 2011). At the embryonic stage, Pdx-1 is essential for pancreatic development and it is expressed in endocrine and exocrine tissues. However, after birth, Pdx-1 is expressed only in pancreatic beta cells and somatostatin cells. Therefore, in the adult pancreas, Pdx-1 does not induce embryonic pancreatic development but it does induce pancreatic beta cell formation by its action to induce insulin gene expression in response to glucose metabolism signaling to the transcriptional machinery (Doiron and DeFronzo, *Int J Endocrinol Metab.* 9:356-357, 2011; Mitanchez et al., *Endo Rev* 18:520-540, 1997). Pdx-1 has been demonstrated in post-development to induce beta cell formation in adult animals (Bouwens and Rooman, *Physiol Rev* 85:1255-1270, 2005). Pdx-1 can be used in the CNIP approach for its post-embryonic action to enhance beta cell formation.

The CNIP approach is designed to induce the post-embryonic development of beta cell formation in the adult pancreas without activation of the embryonic pathway of pancreatic development. Others have used the embryonic pathway or stem cells to recreate the embryologic development of the pancreas. A disadvantage of inducing the embryonic pathway to augment beta cell formation is that it induces all of the endocrine cell types, including glucagon-producing alpha cells that have been shown to play an important pathogenic role in the glucose intolerance of both type 1 diabetes and type 2 diabetes mellitus. The CNIP approach bypasses the embryonic pathway and stem cell pathway to induce pancreatic beta cell formation in the adult pancreas.

Pdx-1 expression and translocation from the cytoplasm to the nucleus are induced by glucose metabolism signaling to the transcriptional machinery (Mitanchez et al., *Endo Rev* 18:520-540, 1997). As described, glucose metabolism is essential for beta cell formation. To create a cell type, the genetic expression profile of the cell has to be changed. Gene induction by glucose metabolism is an example of an epigenetic phenomena in which the gene expression profile is controlled and regulated by the glucose level in the blood (Doiron et al., *J Biol Chem.* 271:5321-5324, 1996; Mitanchez et al., *Endo Rev* 18:520-540, 1997). The Pdx-1 gene expression and translocation from the cytoplasm to the nucleus are induced by glucose metabolism. However, the effect of glucose metabolism signaling is to be directed to the transcriptional machinery involved with the formation of pancreatic beta cells. The overexpression of Pdx-1 will enhance the formation of beta cells by increasing the amount of Pdx-1 that can bind randomly to DNA molecules and find its specific DNA binding site. Thus, overexpression of Pdx-1 plays a central role in converging all of the signaling mechanisms in the CNIP cocktail to stimulate beta cell formation. Overexpression of Pdx-1 in the pancreas results in the convergence of the molecules in the CNIP cocktail to produce beta cells before activating other effects of glucose metabolism signaling on the transcriptional machinery that are not related to beta cell formation (Doiron et al., *J Biol*

Chem. 271:5321-5324, 1996; Mitanchez et al., *Endo Rev* 18:520-540, 1997). The Pdx-1 cDNA has been introduced into a lentivirus construct using the same method described above for lenti-CGK under the control of the CMV promoter. The in vivo methods of injection were used to target the adult mouse pancreas with lenti-CMV-Pdx-1.

Lentivirus CMV-Pdx-1 construct (FIG. 2, B): The mouse PDX-1 genes were subcloned to pEntCMV-WPRE vector and inserts were verified by DNA sequencing. The pENT-PDX-1 were treated with LR Clonase II enzyme (Invitrogen) and ligated to a pLenti vector. The recombination products were transformed into *E. coli* cells. After incubation overnight, the positive clones were selected, and plasmid DNA was purified.

The pEnt-PDX1 and pLenti-PDX1 were transfected into 293 cells. 48 hours after transfection, the cells were lysed in SDS-PAGE buffer and subjected to 4-20% SDS-PAGE gel electrophoresis and Western blot analyses. The Western blot was carried out using the anti-Myc (for PDX1 construct) antibody at a 1:1000 dilution, followed by a HRP conjugated secondary antibody. Antibody binding was detected using ECL reagents.

Figure 4:
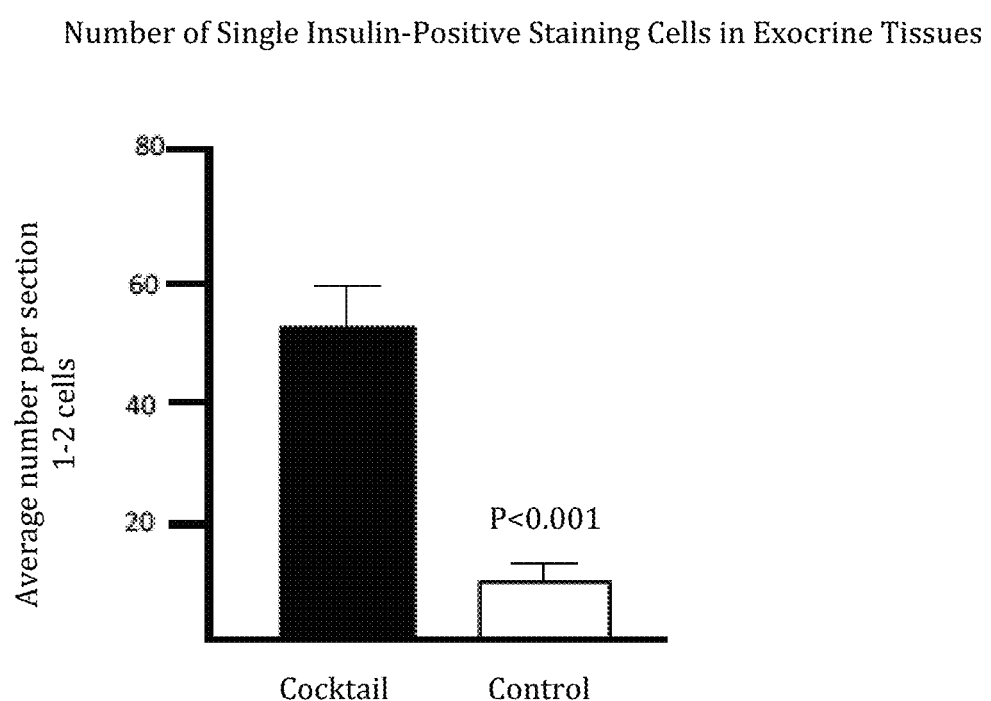
FIG. 4. Quantitation of single beta cell staining in the adult pancreatic tissue in mice injected with a beta cell formation cocktail compared with a control group injected with placebo cocktail.

The number of single or two insulin-positive cells in the exocrine tissues were used as an indication of beta cell formation by comparing the therapeutic group to the control group (FIG. 4). An increase of single or two insulin-positive cells were detected in the exocrine tissues for the therapeutic group.

Figure 5:
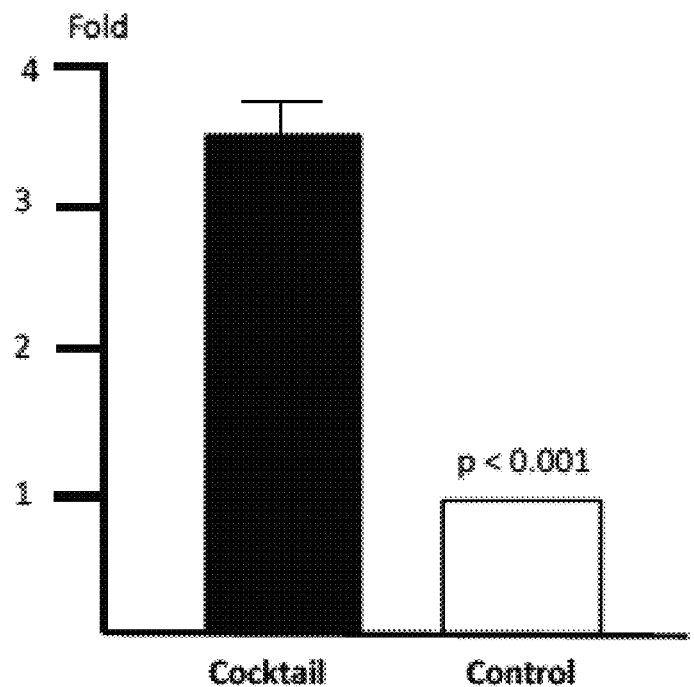
FIG. 5. An example of a beta cell formation cocktail comprising three molecules (GK, PTP1B inhibitor, and Pdx-1) induced proliferation in the adult mouse pancreas compared with the control adult mouse group injected with placebo.

The increase in single or two insulin positive cells in the therapeutic group compared with the control was correlated with the increase in beta cell proliferation, quantitated by the marker BrdU (FIG. 5). The BrdU marker demonstrated proliferation in islets and exocrine tissues.

Co-localization of the proliferation marker BrdU with insulin positive cell demonstrates the formation of new pancreatic beta cells in the group injected with the therapeutic composition. Only pancreatic beta (insulin) cell proliferation was observed. No alpha (glucagon) or delta (somatostatin) cell proliferation was detected. By histologic quantification, the therapeutic composition induced pancreatic beta cell formation. Indeed, as explained above, the therapeutic composition was designed to induce the post-embryonic formation of pancreatic beta cells without causing the formation of glucagon or somatostatin cells.

Figure 6:
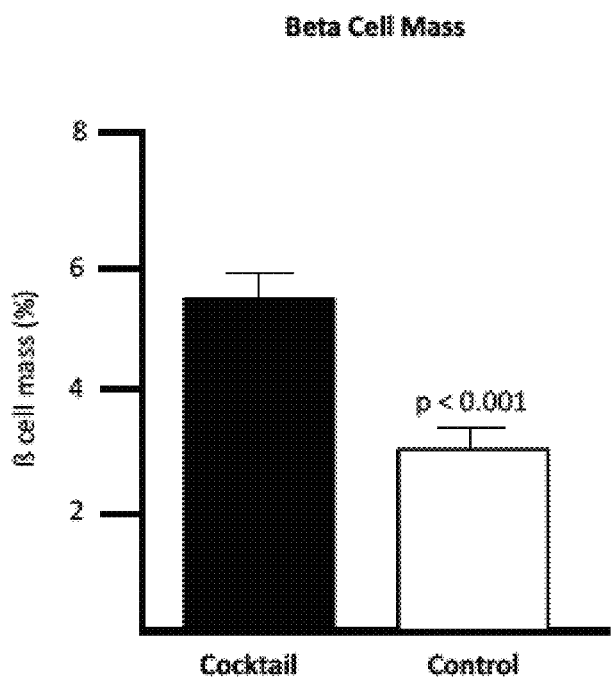
FIG. 6. Pancreatic beta cell mass was significantly increased in adult mice injected with a beta cell formation cocktail (GK, PTP1B inhibitor, and Pdx-1) compared with the control adult mice group injected with the placebo. Immunofluorescence images of insulin staining were captured using confocal microscopy. The beta cell and total pancreatic areas were quantified with Image J (NIH, Bethesda Md.). Total beta cell mass was calculated as the total beta cell area expressed as a percentage of the total area of the pancreas.

Beta cell mass was quantified in the therapeutic and control groups (FIG. 6). Pancreatic beta cell mass was significantly increased in adult mice injected with the therapeutic composition compared with the control adult mice group injected with the control placebo.

Figure 7:
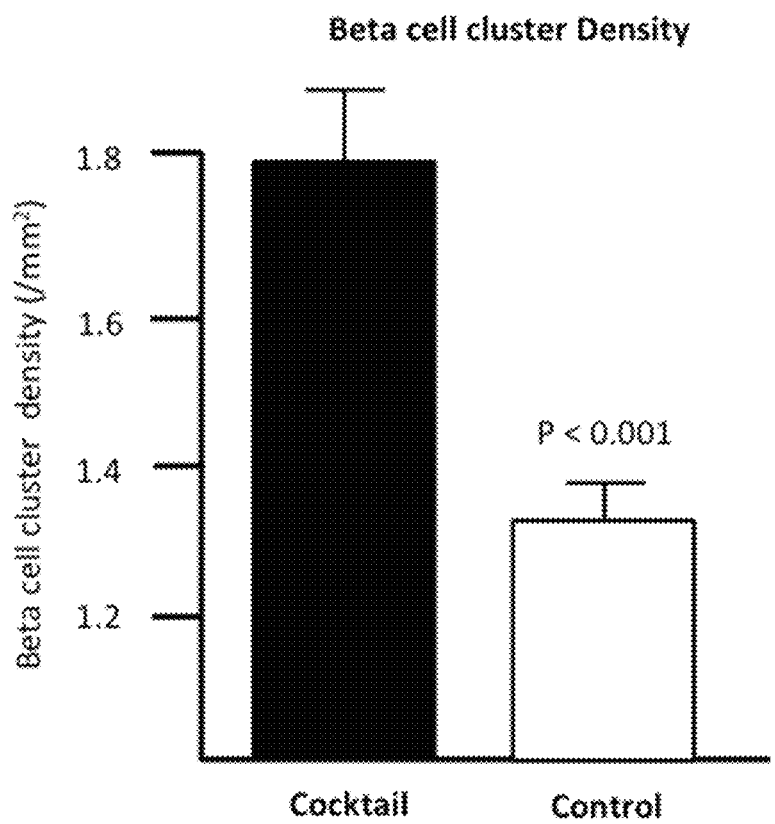
FIG. 7. Illustrates the number of beta cell clusters in the pancreas (cluster density) in the adult mouse group injected with the beta cell formation cocktail compared with the control adult mouse group injected with the placebo. Cluster density was determined as the number of beta cell clusters divided by the total area of the pancreas.

Beta cell cluster density in therapeutic group and control group was quantified. The therapeutic composition caused a significant increase in beta cell cluster density compared to the control (FIG. 7).

Figure 8:
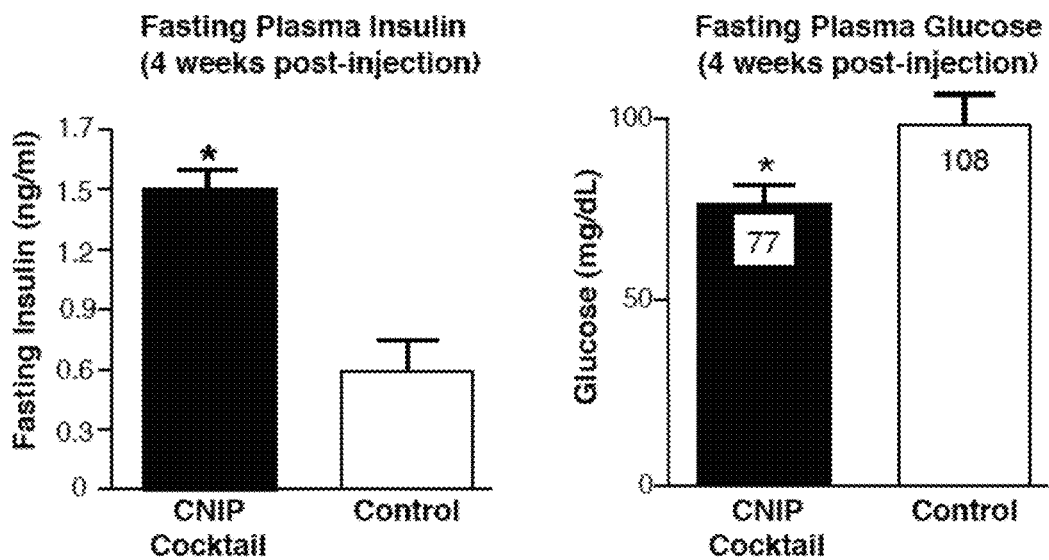
FIG. 8. Illustrates the fasting plasma insulin concentration in the adult mouse group injected with a beta cell formation cocktail (GK, PTP1B inhibitor, and Pdx-1) compared with the adult mouse control group injected with placebo.
Figure 9:
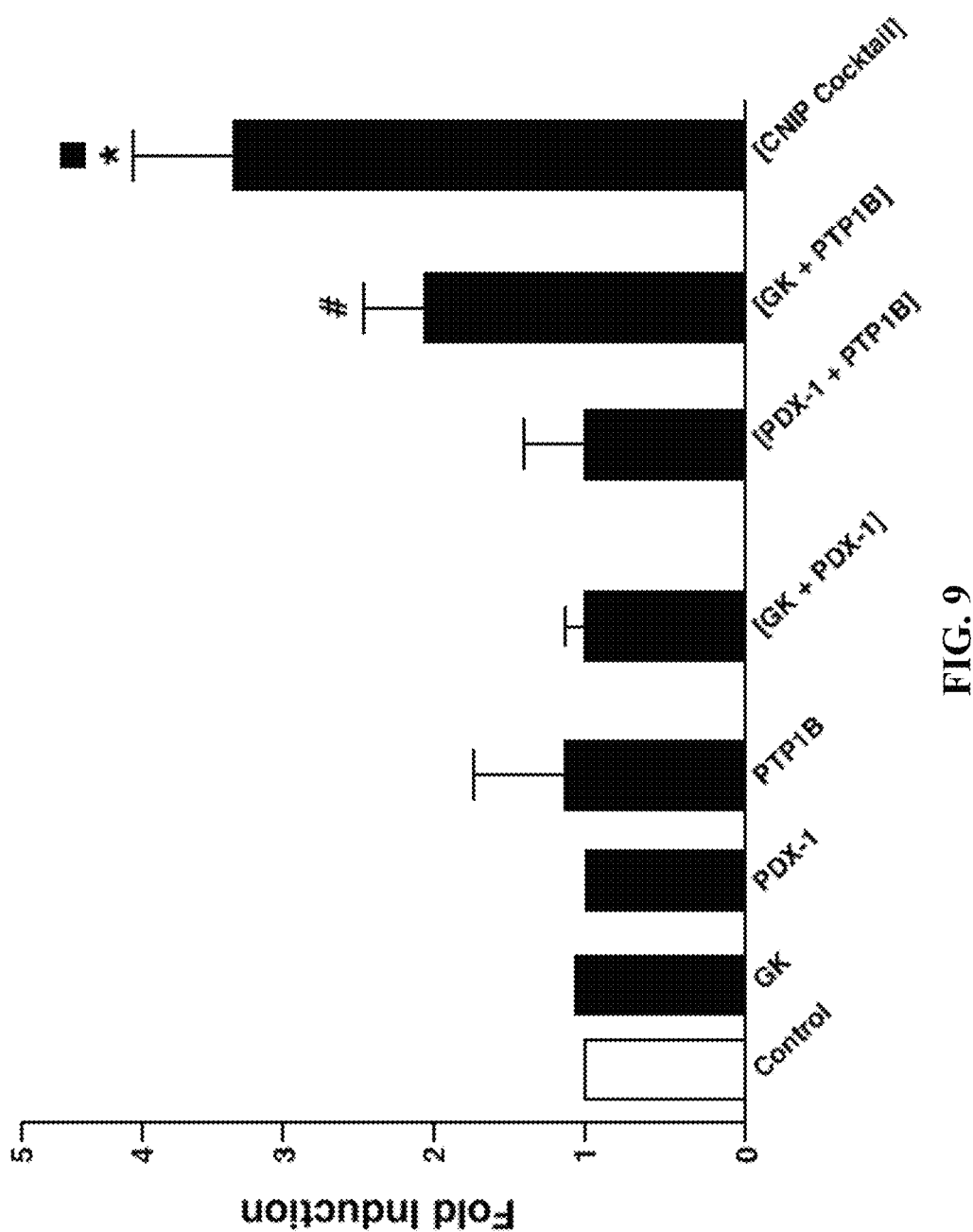
FIG. 9 BrdU marker of proliferation in islets and exocrine tissue 4 weeks post-injection of the cocktail (Lenti-GCK+ Lenti-Pdx-1+Lenti-shRNA PTP1B) or by two molecules or each molecule individually. The figure is representative of an area of the pancreas examined in ten sections per animal (n=3 to 4 for each group), separated by 200 am. The results are expressed as the fold-increase in number of BrdU-labeled cells compared with controls. Confocal laser microscopy was used for analysis. Lenti=Lentivirus; GCK= glucokinase; PTP1B=protein-tyrosine phosphatase 1B. Data are presented as mean±SE. *=$p<0.001$ CNIP cocktail vs control; ■=$p<0.05$ CNIP cocktail vs [GK+PTP1B]; #= $p<0.01$ [GK+PTP1B] vs control.
Figure 10:
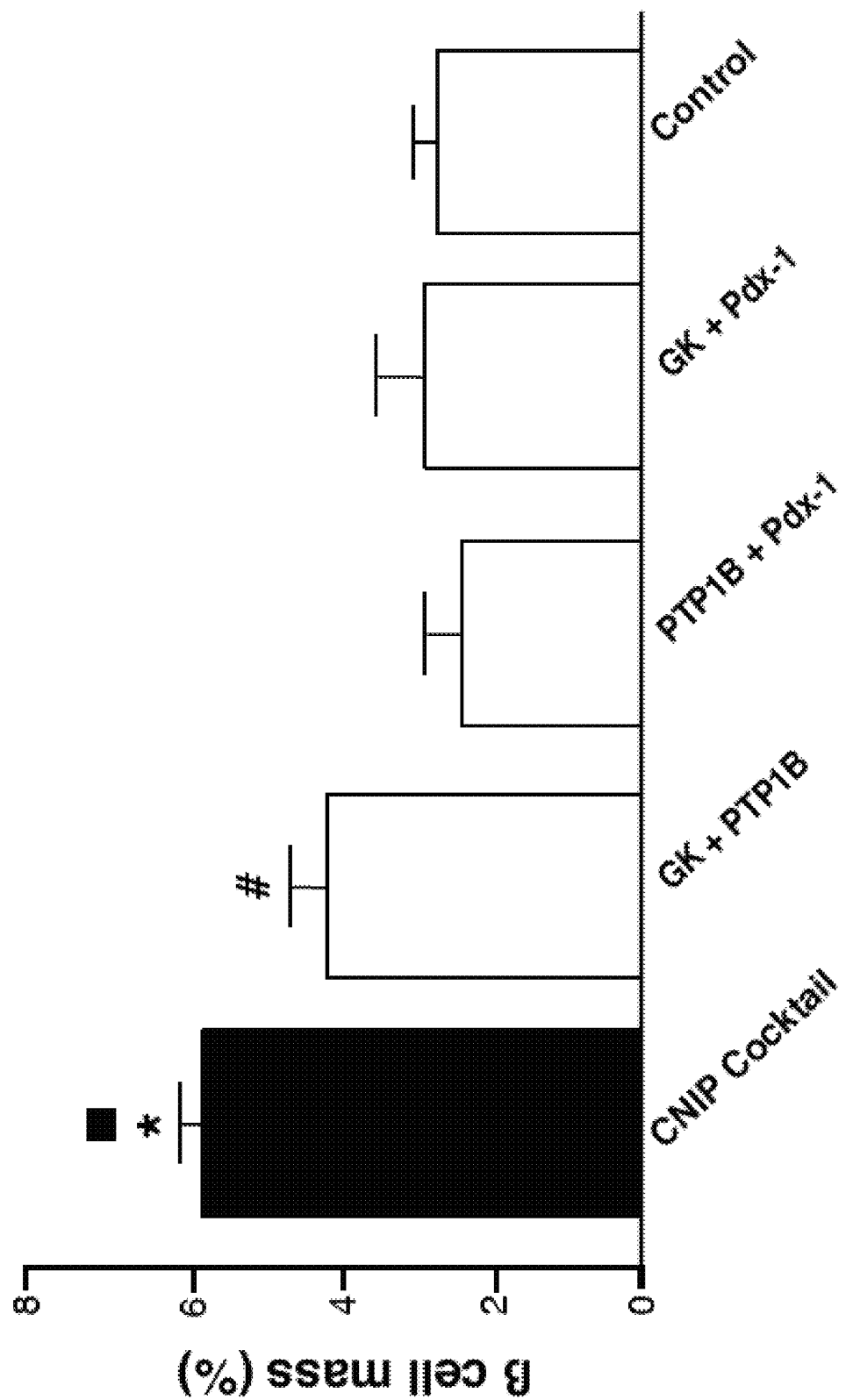
FIG. 10 Beta cell mass 4-weeks post-injection with the cocktail CNIP (Lenti-GCK+Lenti-Pdx-1+Lenti-shRNA PTP1B) or by two molecules or each molecule individually compared to cocktail control and each other (n=3 to 4 for each group). Total pancreatic and insulin positive staining areas of each section were measured using Image J (NIH, Bethesda, USA). Beta cell mass was calculated as the ratio of total insulin positive area to total pancreatic area of all sections, multiplied by the pancreatic tissue wet weight. The figure is representative of an area of the pancreas examined in ten sections per animal, separated by 200 am. Confocal laser microscopy was used for analysis. Lenti=Lentivirus; GCK=glucokinase; PTP1B=protein-tyrosine phosphatase 1B. *=p<0.001=CNIP cocktail vs control; p<0.001 CNIP cocktail vs [GK+Pdx-1]; p<0.001 CNIP cocktail vs [PTP-1B+Pdx-1]; =p<0.05 CNIP cocktail vs [GK ■ +PTP1B]. #=p<0.05 [GK+PTP1B] vs [PTP1B+Pdx-1); p<0.05 [GK+PTP1B] vs control. Data are presented as mean±SE.

The increase in of pancreatic beta cell proliferation, beta cell mass, and beta cell cluster density was correlated with an increase in insulin production after overnight fasting in adult mice injected with the therapeutic composition compared to the control placebo group (FIG. 8).

B. Methods

In Vivo Method for Targeting Gene Delivery to Adult Pancreas:

To study beta cell formation in the adult animal, the adult pancreas was targeted in vivo using a viral vector. The methodology has been validated (Doiron et al., *Diabetologia* 55:719-728, 2012) and employed in the CNIP approach to generate pancreatic beta cells in vivo.

An advantage of lentiviral vectors is that they do not activate dendritic cells to a significant extent. Furthermore, lentiviral vectors can (i) infect and integrate into both dividing and nondividing cells, (ii) provide high transduction efficiency and sustain gene expression in vivo, (iii) do not induce a significant host immune response, and (iv) can be successfully readministered. Importantly, the method of viral vector injection in vivo into the adult mouse pancreas permits one to evaluate new treatments and/or potential cures for a chronic disease that develops in adulthood and avoids the development of compensatory mechanisms that occur when a gene is deleted during embryonic development. This approach obviates some of the paradoxical findings that have been reported with knock out models, i.e. normal/near-normal muscle insulin sensitivity in mice in whom the insulin receptor is knocked out (See Kitamura et al., *Annu. Rev. Physiol.*, 65:313-32, 2003) and the homozygous null mutant for GLUT4 (GLUT4−/−)(See Minokoshi et al., *Journal of Biol. Chem.*, 278(36): 33609-12, 2003), which did not manifest a diabetic phenotype. Therefore, in certain embodiments a lentiviral vector is used to target the pancreas directly.

Figure 3:
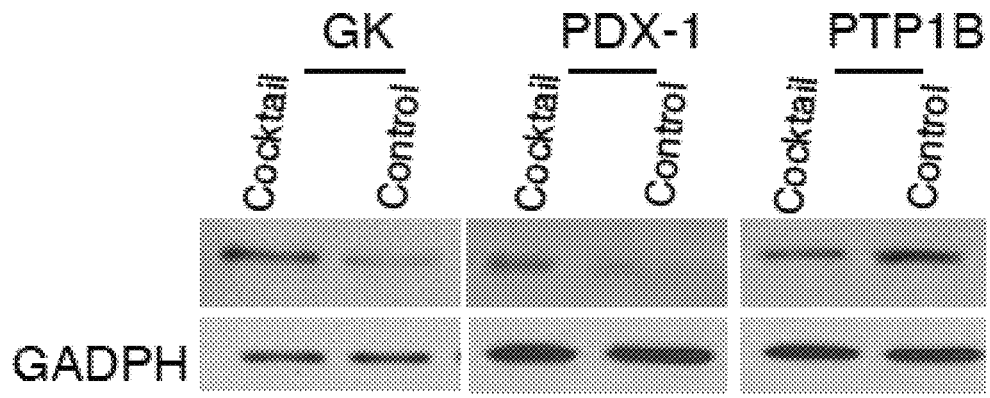
FIG. 3. In vivo over-expression of PDX-1 and GK, and suppression of PTP1B expression by the CNIP cocktail (Lenti-GCK+Lenti-Pdx-1 and Lenti-shRNA PTP1B).

In brief, a lentiviral construct can be introduced into the mouse pancreas via the intraductal route, as follows: a 32-gauge catheter (Braintree Scientific, Inc, Braintree, Mass.) is inserted into the cystic duct through a small opening in the gallbladder. The catheter is then advanced into the common bile duct and secured in place with a slipknot of 0/0 suture around the bile duct and catheter to prevent vector reflux into the liver. With a micro clamp placed around the sphincter of Oddi to avoid leakage of the vector into the duodenum, 100 µl lentiviral vector expressing green fluorescent protein (GFP) at $10^8$ TU/ml is slowly injected into the pancreatic duct through the catheter. Two weeks post-infection, the entire pancreas is removed for histological examination. After 48 hours, injection of lentivirus coding for GFP under the control of cytomegalovirus (CMV) promoter specifically targeted the pancreatic tissues (Doiron et al., 2012). Quantitative morphometric analysis of pancreatic transduction by the lentivirus vector, based on GFP expression, showed that 60% of the tissue expressed GFP. Expression was detected in the pancreas even after four weeks (FIG. 3). The lentivirus vector expressed green fluorescent protein was not found in any other tissues in the body including heart, lung, liver, brain, leg muscle, and kidney by histology and PCR (data not shown). Pancreatic tissue was stained with H&E to look for evidence of inflammation (pancreatitis) at day 2 and day 14 post-injection. No evidence of inflammation was observed. Following the lentiviral vector injection containing shRNA Grb10 or shRNA scramble, activity, daily food intake over the 14 days post-injection; (shRNA scramble mice, 5.4±0.3 grams/day [n=5] versus shRNA Grb10 mice, 5.9±0.5 grams/day [n=6]), and weight gain were similar in the shRNA Grb10 and shRNA scramble groups. No diarrhea was observed in either the control or experimental groups after the lentivirus injection, and pancreatic (lipase) and hepatic (AST, ALT) enzymes were not elevated (Doiron et al., *Diabetologia* 55:719-728, 2012). These results demonstrate that lentivirus injection technique does not cause adverse gastrointestinal, pancreatic, or hepatic effects.

The inventors also constructed and produced a lentivirus expressing glucokinase (GK), Pdx-1 transcriptional factor, and shRNA targeting PTP1B. Male C57BL/6 mice (Charles River, Wilmington, Mass., USA) 8 weeks of age were used and maintained on an ad libitum diet of water and normal chow for all experiments. At day 1 post-injection with lentiviral vector, the mice were injected i.p. daily with BrdU (Sigma-Aldrich, St Louis, Mo., USA) in PBS at a dose of 50 µg/g body weight for 12 days to quantitate beta cell proliferation. At 4 weeks post-lentiviral injection, the entire pancreas was removed for histological examination.

Direct administration to the adult pancreas in vivo can be used to over-produce a protein(s) or to suppress production of a protein(s). In summary, the inventors have developed a methodological protocol to target the adult pancreas in vivo. The technique will be employed in validation studies of the CNIP approach to promote beta cell formation. The lentivirus injection method described above provides proof of concept that adult pancreas can be targeted directly. The data obtained using the lentivirus approach to target/generate pancreatic beta cells can be modified using small molecules and non-viral therapeutics.

Animal Studies:

Males C57BL/6 mice (Charles River, Wilmington, Mass., USA) 8 weeks of age were used and maintained on a diet of water and normal chow ad libitum for all experiments. At 1 day post-injection with lentiviral vector, the mice were injected i.p. daily with BrdU (Sigma-Aldrich, St Louis, Mo., USA) in PBS at a dose of 50 µg/g body weight for 12 days. At 4 weeks post-lentiviral injection, the entire pancreas was removed for histological examination (see below).

Immunofluorescent and Immunohistochemical Analysis:

Adult mouse pancreatic tissues were fixed by immersion in phosphate buffer 4% paraformaldehyde-1% glutaraldehyde overnight at 4° C. and subsequently embedded with Tissues-Tek OCT compound for cryostat sectioning. The following primary antibodies were used: anti-somatostatin (G-10), anti-Ki-67 (M-19), anti-glucagon (K79bB10) and anti-insulin A (C-12), antibodies and control rabbit IgG (Santa Cruz Inc., Santa Cruz, Calif., USA). For proliferation studies, pancreatic tissues were stained with either Ki67 (M-19) antibody (Santa Cruz Inc., Santa Cruz, Calif., USA) or with rat monoclonal BrdU antibody (Abcam Inc., Cambridge, Mass., USA). Antigen retrieval was performed for Ki67 and BrdU antibodies by boiling sections for 10 min in 10 mM citrate buffer followed by cooling for 30 min to room temperature. Nuclei were counterstained with DAPI (Vector Laboratories, Inc., Burlingame, Calif., USA). The fluorescent secondary antibodies used included donkey anti-goat-fluorescein, goat anti-mouse-fluorescein, goat anti-rabbit Texas red, and donkey anti-goat Texas red (Santa Cruz Inc., Santa Cruz, Calif., USA). The beta cell area represents the surface area of cells staining positively for insulin immunostaining divided by the total pancreatic surface scanned with Olympus FV-1000 laser scanning confocal microscope. The insulin positive and total pancreatic areas were quantified with Image J (National Institutes of Health, Bethesda, Md., USA). Beta cell mass was calculated as beta-cell area multiplied by pancreatic wet weight. At least three mice were analyzed per condition. Pancreatic tissue was stained with H & E to look for evidence of inflammation (pancreatitis) at day 2 and day 14 post-injection of the Lentivirus.

Western Blot:

For western blots, equal amounts of total protein were separated on a 10 and 15% SDS/PAGE and transferred onto nitrocellulose membranes. Membranes were then blocked with 5% nonfat milk in 0.1% TBS Tween-20 and probed with specific antibodies against Pdx-1 (Cell Signaling Technology, Danvers, Mass., USA), PTP1B (Abcam Inc., Cambridge, Mass., USA), glucokinase (Santa Cruz Inc, Santa Cruz, Calif., USA), and GAPDH (G9545, Sigma Aldrich, St Louis, Mo., USA). Membranes were then incubated with HRP-conjugated secondary antibody (NA934) and developed with a chemiluminescent reagent (Amersham Bioscience, GE Healthcare, Pittsburgh, Pa., USA).

Statistical Analysis:

Results are presented as mean±SEM. Statistical comparisons were performed with Student's unpaired t test or one-way ANOVA, where appropriate. Results were considered to be statistically significant when $p<0.05$.

The invention claimed is:

1. A method for inducing beta cell formation of cells in vitro or in vivo comprising: providing a mammalian cell with a combination of (i) a first agent that increases glucokinase (GK) levels, (ii) a second agent that increases tyrosine receptor kinase activity and/or tyrosine kinase associated receptor activity, and (iii) a third agent that increases Pdx-1 mediated transcription, thereby inducing beta cell formation.

2. The method of claim 1, wherein the mammalian cell is a pancreatic cell, a liver cell, a gut K cell, a neuron, or a stem cell.

3. The method of claim 1, wherein the induction of beta cell formation is in vitro.

4. The method of claim 1, further comprising implanting the induced beta cell into a subject to be treated.

5. A method for inducing beta cell formation from pancreatic cells in vivo comprising: providing to a pancreas in vivo, a combination of (i) a first agent that increases glucokinase (GK) levels, (ii) a second agent that increases tyrosine receptor kinase activity and/or tyrosine kinase associated receptor activity, and (iii) a third agent that increases Pdx-1 mediated transcription in pancreatic cells, thereby inducing beta cell formation.

6. The method of claim 5, wherein the first agent is a nucleic acid encoding glucokinase.

7. The method of claim 6, wherein the nucleic acid encoding glucokinase is further comprised in a viral vector.

8. The method of claim 7, wherein the viral vector is a lentivirus vector.

9. The method of claim 7, further comprising a posttranscriptional regulatory element of woodchuck hepatitis virus (WPRE) 3' of the coding sequence.

10. The method of claim 5, wherein the first agent is small molecule activator of glucokinase.

11. The method of claim 10, wherein the small molecule activator of glucokinase is R1440, R00281675, R04389620 (Piragliatin), LY2121260, PSN-GK1, or GKA-50.

12. The method of claim 5, wherein the second agent is an inhibitor of protein tyrosine phosphatase 1B.

13. The method of claim 12, wherein the protein tyrosine phosphatase 1B (PTP1B) inhibitor is an shRNA inhibitor of protein tyrosine kinase phosphatase 1B or a PTP1B antisense DNA.

14. The method of claim 12, wherein the protein tyrosine phosphatase 1B inhibitor is antisense ISIS-PTP1BRX; or (S)-isothiazolidinone ((S)-IZD) heterocyclic phosphotyrosine.

15. The method of claim 5, wherein the third agent is a nucleic acid encoding Pdx-1.

16. The method of claim 5, wherein the first, second, and third agent are provided by injection of the pancreas through the pancreatic duct.

17. A method of treating type 1 or type 2 diabetes comprising: providing a therapeutic composition to a pancreas in vivo comprising (i) glucokinase expression cassette configured to express a functional glucokinase protein in a pancreatic cell, (ii) a tyrosine phosphatase 1B inhibitor, and (iii) a Pdx-1 expression cassette configured to express a functional Pdx-1 protein in a pancreatic cell, wherein pancreatic beta cells are induced in the pancreas and type 1 or type 2 diabetes is treated.

18. The method of claim 17, wherein diabetes is type 1 diabetes.

* * * * *